United States Patent [19]

Blasberg et al.

[11] Patent Number: 5,703,056
[45] Date of Patent: Dec. 30, 1997

[54] NON-INVASIVE IMAGING OF GENE TRANSFER

[75] Inventors: Ronald G. Blasberg, Riverside, Conn.; Juri Tjuvajev, Brooklyn, N.Y.

[73] Assignee: Sloan-Kettering Institute for Cancer Research, New York, N.Y.

[21] Appl. No.: 404,513

[22] Filed: Mar. 15, 1995

[51] Int. Cl.$^6$ .............................. A01N 43/04; A61K 31/70
[52] U.S. Cl. .................. 514/44; 435/172.3; 435/172.1; 435/320.1; 435/194; 436/504; 600/9; 600/1; 600/2; 600/3; 600/4; 536/23.2; 536/23.5; 536/23.74; 536/23.1
[58] Field of Search .......................... 514/44; 536/23.2, 536/23.5, 23.74, 23.1; 435/320.1, 172.1, 172.3, 194; 436/504; 600/9, 1, 2, 3, 4

[56] References Cited

PUBLICATIONS

Emiliana Borrelli, Richard Heyman, Mary Hsi and Ronald M. Evans, "Targeting of an inducible toxic phenotype in animal cells," Proc. Natl. Acad. Sci. U.S.A., 85, 7572–7576 (1988); U.S.A.

Kenneth W. Culver and R. Michael Blaese, "Gene therapy for cancer," Trends in Genetics, 10, 174–178 (1994); U.S.A.

Kenneth W. Culver, Zvi Ram, Stuart Wallbridge, Hiroyuki Ishii, Edward H. Oldfield and R. Michael Blaese, "In Vivo Gene Transfer with Retroviral Vector–Producer Cells for Treatment of Experimental Brain Tumors," Science, 256, 1550–1552 (1992); U.S.A.

Marston Manthorpe, Racine Cornefert-Jensen, Jukka Hartikka, Jiin Felgner, Ann Rundell, Michal Margalith and Varavani Dwarki,"Gene Therapy by Intramuscular Injection of Plasmid DNA: Studies on Firefly Luciferase Gene Expression in Mice," Human Gene Therapy, 4, 419–431 (1993); U.S.A.

Yutaka Saito, Richard W. Price, David A. Rottenberg, Jack J. Fox, Tsann–Long Su, Kyoichi A. Watanabe and Frederick S. Philips, "Quantitative Autoradiographic Mapping of Herpes Simplex Virus Encephalitis with a Radiolabled Antiviral Drug," Science, 217, 1151–1153 (1982); U.S.A.

Frederick L. Moolten, "Tumor Chemosensitivity Conferred by Inserted Herpes Thymidine Kinase Genes: Paradigm for a Prospective Cancer Control Strategy, " Cancer Research 46, 5276–5281 (1986); U.S.A.

Frederick L. Moolten and John M. Wells, "Curability of Tumors Bearing Herpes Thymidine Kinase Genes Transferred by Retroviral Vectors," Journal of the National Cancer Institute, 82, 297–300 (1990); U.S.A.

Frederick S. Phillips, Aaron Feinberg, Ting–Chao Chou, Pedro M. Vidal, Tsann–Long Su, Kyoichi A. Watanabe and Jack J. Fox, "Distribution, Metabolism, and Excretion of 1–(2–Fluoro–2deoxy–B–D–arabinofuranosyl) thymine and 1–(2–Fluoro–2–deoxy–B–D–arabinofuranosyl) –5–iodocytosine," Cancer Research 43, 3619–3627 (1983); U.S.A.

Kendall O. Smith, Karen S. Galloway, Wiebke L. Kennell, Kevin K. Ogilvie and Bruno K. Radatus, "A New Nucleoside Analog, 9–(2–Hydroxymethyl) Ethoxy Methyl Guanine, Highly Active In Vitro Against Herpes Simplex Virus Types 1 and 2," Antimicrobial Agents and Chemotherapy, 22, 55–61 (1982); U.S.A.

Juri G. Tjuvajev, Homer A. Macapinlac, Farhad Daghighian, Andrew M. Scott, James Z. Ginos, Ronald D. Finn, Paresh Kothari, Revathi Desai, Jiaju Zhang, Bradley Beattie, Martin Graham, Stevin M. Larson and Ronald G. Blasberg, "Imaging of Brain Tumor Proliferative Activity with Iodine–131–Iododeoxyuridine," Journal of Nuclear Medicine, 35, 1407–1417 (1994); U.S.A.

Kyoichi A. Watanabe, Uri Reichman, Kosaku Hirota, Carlos Lopez and Jack J. Fox, "Nucleosides, 110. Synthesis and Antiherpes Virus Activity of Some 2'–Fluoro–2'–deoxy–arabinofuranosylpyrimidine Nucleoides," Journal of Medicinal Chemistry, 22, 21–24 (1979); U.S.A.

Singleton et al. (eds.) 1987 in: Dictionary of Microbiology and Molecular Biology, Second Edition, John Wiley & & Sons, Chichester,GB, pp. 901–904.

Froguel et al. 1995 Tibtech, 52–55.

Biological Abstracts, 90(11): AB–1214, abstract number 129728, Martelli et al. 1990, Pharmacol. Toxicol. 66(5): 329–334.

Biological Abstracts, 91(12): AB–175, abstract number 127575, Loft et al., 1991, Biochem. Pharmacol. 41(8): 1127–1134.

Biological Abstracts, 81: AB–685, abstract number 103868, Heimbrook et al. 1986, Mol. Pharmacol. 29(2): 168–172

Primary Examiner—Christopher S.F. Low
Attorney, Agent, or Firm—John P. White

[57] ABSTRACT

The subject invention provides a method of detecting gene transfer to and expression in a target tissue of a host subject comprising: (a) administering to the host subject a transfer vector containing a marker gene not naturally present in the host and nontoxic to the host, wherein the transfer vector transfects cells of the target tissue, under conditions such that the marker gene is expressed in transfected cells of the target tissue, thereby generating a marker gene product; (b) administering to the host subject a labelled marker substrate which is not metabolized by non-transfected cells, under conditions such that the marker substrate is metabolized by the marker gene product of step (a) to produce a labelled marker metabolite which is substantially retained in the transfected cells throughout a time-period sufficient for imaging the labelled marker metabolite; and (c) imaging the labelled marker metabolite, thereby detecting gene transfer to and expression in the target tissue. The subject invention provides a non-invasive, clinically applicable method for imaging gene transfer and expression which can be implemented using existing imaging techniques to monitor and evaluate in vivo gene therapy in human subjects.

13 Claims, 15 Drawing Sheets

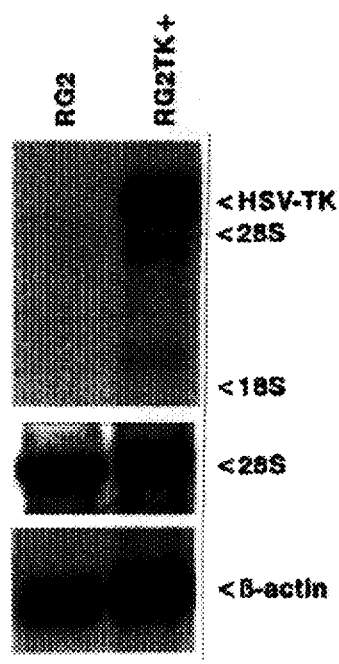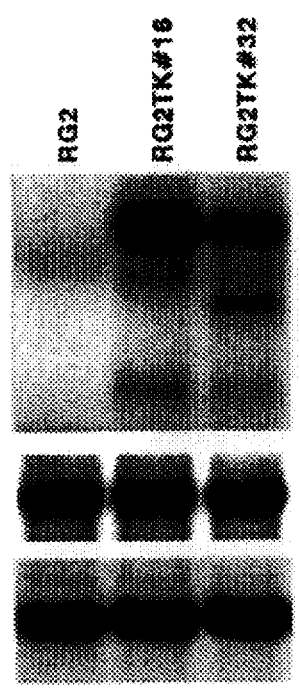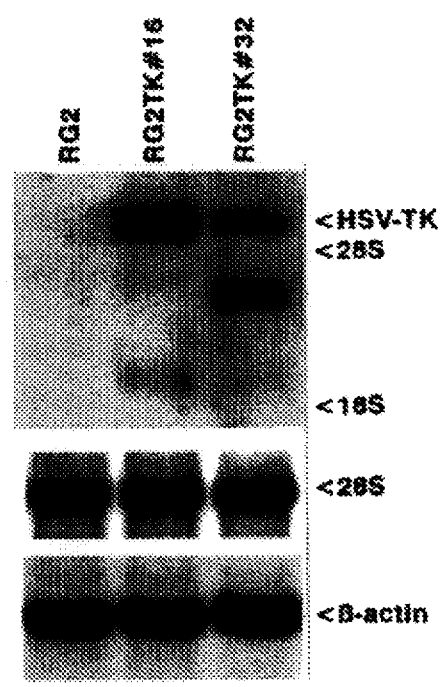

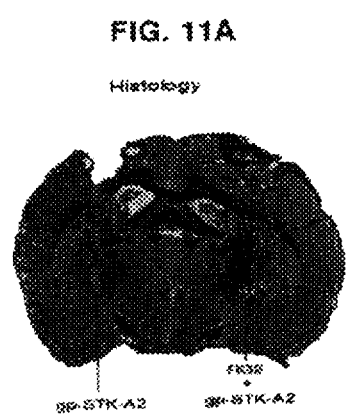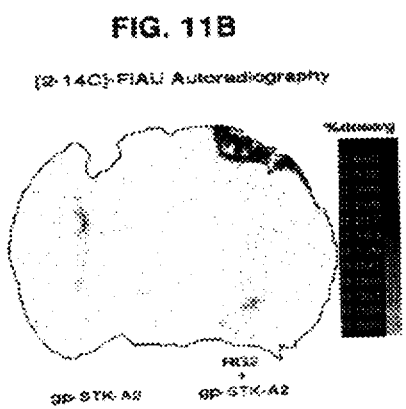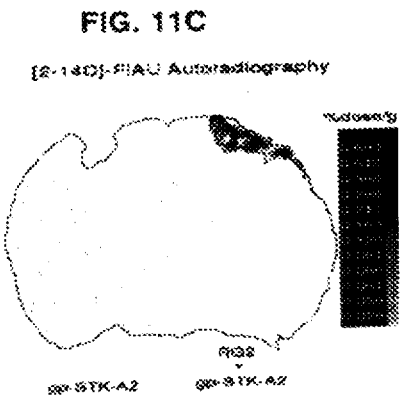
FIG. 11A Histology   FIG. 11B [2-14C]-FIAU Autoradiography   FIG. 11C [2-14C]-FIAU Autoradiography

FIG. 12A
Histology
FIG. 12B
[2-14C]-FIAU Autoradiography
FIG. 12C
[2-14C]-FIAU Autoradiography
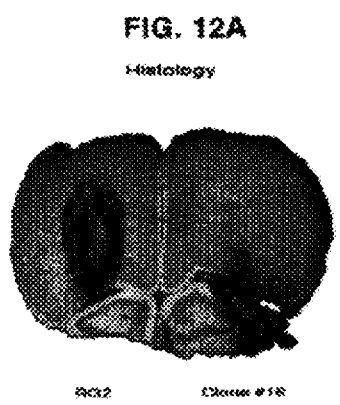
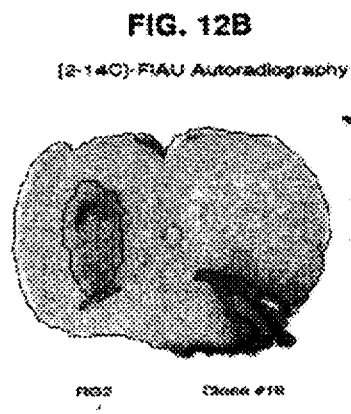
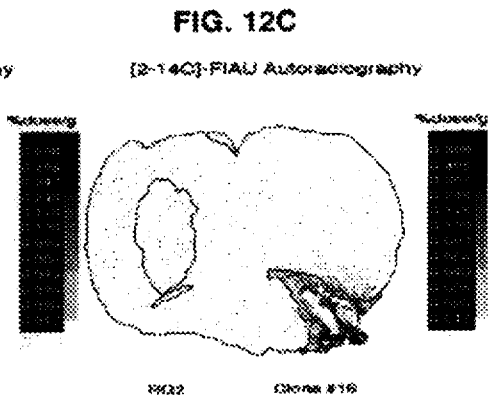

NON-INVASIVE IMAGING OF GENE TRANSFER

BACKGROUND OF THE INVENTION

This invention relates to methods of monitoring gene transfer and of monitoring the treatment of disease by gene transfer.

Gene therapy for the treatment of human disease is currently being evaluated and several approaches are being tested in patients. [Culver, K. W., and Blaese, R. M., Trends in Genetics, 10: 174–8, 1994; Cancer Gene Therapy, 1 (4): 291, 1994; A non-invasive, clinically applicable method for imaging successful gene transfer and expression in target tissue or specific organs of the body would be of considerable value; it would facilitate the monitoring and evaluation of gene therapy in human subjects by defining the location, magnitude and persistence of gene expression over time.

Gene therapy. The increasing knowledge of the genetics and molecular biology of human disease, particularly in human cancer, has led to the application of new biological approaches in therapy. A limitation of many biological-based therapies has been an inability to achieve controlled and effective delivery of biologically active molecules to tumor cells or their surrounding matrix. This condition is particularly limiting for biologically active compounds that have very short half-lives and exhibit site-specific therapeutic and toxic effects. For example, many cytokines exhibit very short biological half-lives and manifest considerable toxicity following systemic administration. This often limits the dose that can be administered and the therapeutic effect that can be achieved. In other cases, agents such as tumor suppressor proteins or xenoantigens are effective only at or within specific compartments of the cell, and cannot usually be targeted with conventional systemic or local drug administration. The aim of employing gene-based therapy is to achieve effective delivery of biological products, as a result of gene expression, to their site of action within the cell. Gene-based therapy can also provide control over the level, timing and duration of action of these biologically active products by including specific promoter/activator elements in the genetic material transfered resulting in more effective therapeutic intervention. Methods are actively being developed for controlled gene delivery to various somatic tissues and tumors using novel formulations of DNA, and for controlling gene expression using cell specific, replication-activated and drug-controlled expression systems. [Jolly, D. Cancer Gene Therapy, 1 (1): 51–64, 1994]

Current gene-based therapies for cancer involve several different biological approaches to treatment and new approaches continue to be developed. There are 64 human gene-therapy clinical trials currently being investigated in the U.S., and additional studies are being performed in Europe and Asia. Included are 27 "immunotherapy/cytokine" protocols, most of which involve the transfer of cytokine genes into tumor cells. There are 9 "drug sensitivity" protocols; they include five protocols for the treatment of brain tumors, and four other protocols for the treatment of leptomeningeal carcinomatosis, persistent head and neck cancer, advanced mesothelioma, and ovarian cancer. [Cancer Gene Therapy, 1 (4): 291, 1994] All 9 involve retroviral transfer of the HSV1-tk gene into tumor cells followed by systemic treatment with ganciclovir™. This approach is based on the fact that certain genes can be used to "sensitize" cells to drugs that are normally inactive or nontoxic (e.g., pro-drugs), and these genes have been described as "suicide" genes. Most "suicide" genes encode viral or bacterial enzymes that convert inactive forms of a drug, pro-drug, into toxic compounds or antimetabolites capable of inhibiting nucleic acid synthesis. Their use in cancer therapy is to create significant differences between normal and malignant cells by selective transduction of the "suicide" gene into malignant, but not normal cells. There are 8 "tumor suppressor (anti-oncogene)/antisense" protocols involving replacement of defective p53 genes, or ribozyme and antisensense targeting of mutant p53, K-ras, c-myc, or c-myb. There are 3 "drug resistence" protocols, all of which involve transfer of multi-drug resistance cDNA. There are also 19 "gene marker" protocols that are primarily designed to assess the efficacy and safety of gene transfer and gene therapy in patients. All these protocols involve transfer of the neomycin resistance gene into lymphocytes or stem cells ex vivo and their readministration to patients. Questions related to the distribution (e.g., blood, bone marrow and surgical specimens) and persistence of the genetically altered cells, identified by their resistance to neomycin toxicity, are being addressed. Tumors being studied include "advanced cancer", melanoma, breast, lymphoid malignancies, neuroblastoma, etc.

It is clear that a rapidly expanding interest in human gene therapy has developed, and that there is a clinical need to be able to monitor the "safety", "success" and "failure" of gene transfer and expression in patients undergoing gene therapy. This is particularly important with the use of replication-deficient viruses as gene transfer gents, and the small but theoretically possible chance of inducing a malignant tumor with a retroviral vector. This is attested to by the 19 protocols (out of a total of 64) that are considered as "gene marker" studies. However, assessment for the neomycin resistance "marker gene" is usually limited to blood or bone marrow specimens; assessments for the presence of cells harboring the gene in solid tumors or organs requires resection or biopsy and is more difficult. It should also be noted that many new gene therapy protocols are in the process of being developed and many new clinical trials will be implemented in the future.

Noninvasive imaging of gene transfer and expression. A non-invasive, clinically applicable method for imaging successful gene transfer and expression in target tissue or specific organs of the body would be of considerable value; it would facilitate the monitoring and evaluation of gene therapy in human subjects by defining the location, magnitude and persistence of gene expression over time. Successful targeting of cells in tissue culture can be assayed in several different ways including direct assays for the gene product or indirect assays for mRNA (Northern blot analysis) and functional assays (e.g., drug sensitivity). These assays require tissue culture techniques or sampled tissue, and therefore have limited application in a clinical setting. They also provide no spatial information with respect to the location of successful gene transfection in specific tissue or organs. Several histochemical techniques have been developed to identify the location of transduced cells and gene expression in tissue sections obtained in animals. The most popular "marker genes" for histochemical assays in tissue sections are the E. coli lacZ gene [Price, J., Turner, D., and Cepko, C. Proc. Natl. Acad. Sci. U.S.A., 84: 156–160, 1987] and the fire-fly luciferase gene. [Manthorpe, M., Cornefert-Jensen, F., Hartikka, J., Felgner, J., Rundell, A., Margalith, M., and Dwarki, V., Human Gene Therapy, 4 (4): 419–31, 1993] No method exists to identify successful gene transduction and expression in patients undergoing gene therapy using noninvasive imaging techniques. The subject invention seeks to address this need and to provide a clinically applicable method for imaging successful gene transfer and expression in target tissue (or organs).

Disclosed herein is a strategy for imaging gene transfer and expression that involves the selection of an appropriate "marker gene" and "marker substrate". The present inventors have determined that the herpes simplex virus thymidine kinase gene (HSV1-tk) is a good "marker gene", and that 2'-fluoro-5-iodo-1-β-D-arabinofuranosyl-uracil (FIAU) can be used as a "marker substrate" for the enzyme HSV1 thymidine kinase (HSV1-TK), the gene product of HSV1-tk. In addition, HSV1-tk is currently being used as a "suicide gene" (in combination with ganciclovir™) in 9 clinical gene therapy protocols for the treatment of various tumors. [Culver, K. W., and Blaese, R. M., Trends in Genetics, 10: 174–8, 1994; Cancer Gene Therapy, 1 (4): 291, 1994] Thus, the subject invention also provides a method of monitoring gene transfer and expression using HSV1-tk as both a "therapeutic" and a "marker" gene.

As disclosed herein, the 2'-fluoro-nucleoside analogues were chosen for use in the subject invention because they are selectively phosphorylated by HSV1-tK, can be radiolabelled with appropriate radionuclides for imaging with SPECT and PET, and are resistant to metabolic degradation in vivo [Abrams, D. N., Mercer, J. R., Knaus, E. E., and Wiebe, L. I., Int. J. Appl. Radiat. Isot., 36: 233–8, 1985], thereby facilitating interpretation of the resultant images and measurements.

BRIEF DESCRIPTION OF THE FIGURES

A more complete understanding of the invention and many of its advantages will become apparent by reference to the detailed description which follows when considered in conjunction with the accompanying figures wherein:

FIGS. 2A, 2B, and 2C show Northern blot analysis of HSV-tk mRNA levels in different cell lines. A) No HSV-tk mRNA is seen in naive RG2 cells and a high level of HSV-tk mRNA is seen in the bulk RG2TK+ cell line. B) The highest level of HSV-tk mRNA expression was observed in the clone #16 and a low level of expression is seen in clone #32. C) Re-hybridized blot of (B) with the MoMLV-U3 probe which recognizes HSV vector-specific RNA transcripts. The amounts of RNA were similar in all lanes as seen by the 28× band and by re-hybridization with the β-actin probe.

FIG. 1) and normalized IOD values of HSV1-tk mRNA (HSV1-tk mRNA IOD divided by IOD of 28S RNA; see FIG. 2) for corresponding cell lines could be described by the equation: $y=222*e^{\wedge}(-0.166\ X)$ (R=0.999) (Panel A). The accumulation of FIAU, expressed as the normalized FIAU/TdR uptake ratio (slope in FIG. 3) was correlated with the normalized IOD values of HSV1-tk mRNA and could be described by the equation: $y=0.0449+0.0861(X)$ (R=0.999) (Panel B). The relationship between FIAU accumulation and sensitivity to ganciclovir™ for corresponding cell lines could be described by the equation: $y=0.325-0.121\log(x)$ (R=0.999) (Panel C).

FIG. 11 shows the efficacy of imaging successful HSV1-tk gene transduction in vivo, 24 h after 2-[14C]-FIAU administration. A) toluidine blue stained histological section; B) gray-scaled quantitative autoradiographic image of 2-[$^{14}$C]-FIAU accumulation expressed as % administered dose per gram of tissue; C) gray scaled images of acid-rinsed adjacent section. The in vivo HSV1-tk gene-transduced RG2(TK+) tumor, produced by co-implantation of RG2 and gp-STK-A2 cells, is located in the right hemisphere; the injection site of the gp-STK-A2 cells is located in the left hemisphere.

FIG. 12 shows the effect of timing on selective imaging of HSV1-TK expression with FIAU, 4 h after tracer administration. A) toluidine blue stained histological section; B) gray-scaled quantitative autoradiographic image of 2-[$^{14}$C]-FIAU accumulation expressed as % administered dose per gram of tissue; C) gray-scaled images of acid-rinsed adjacent section. The in vivo HSV1-tk gene-transduced RG2TK+ tumor, produced by co-implantation of RG2 and gp-STK-A2 cells, is located in the right hemisphere; the injection site of the gp-STK-A2 cells is located in the left hemisphere.

SUMMARY OF THE INVENTION

Figure 1A:
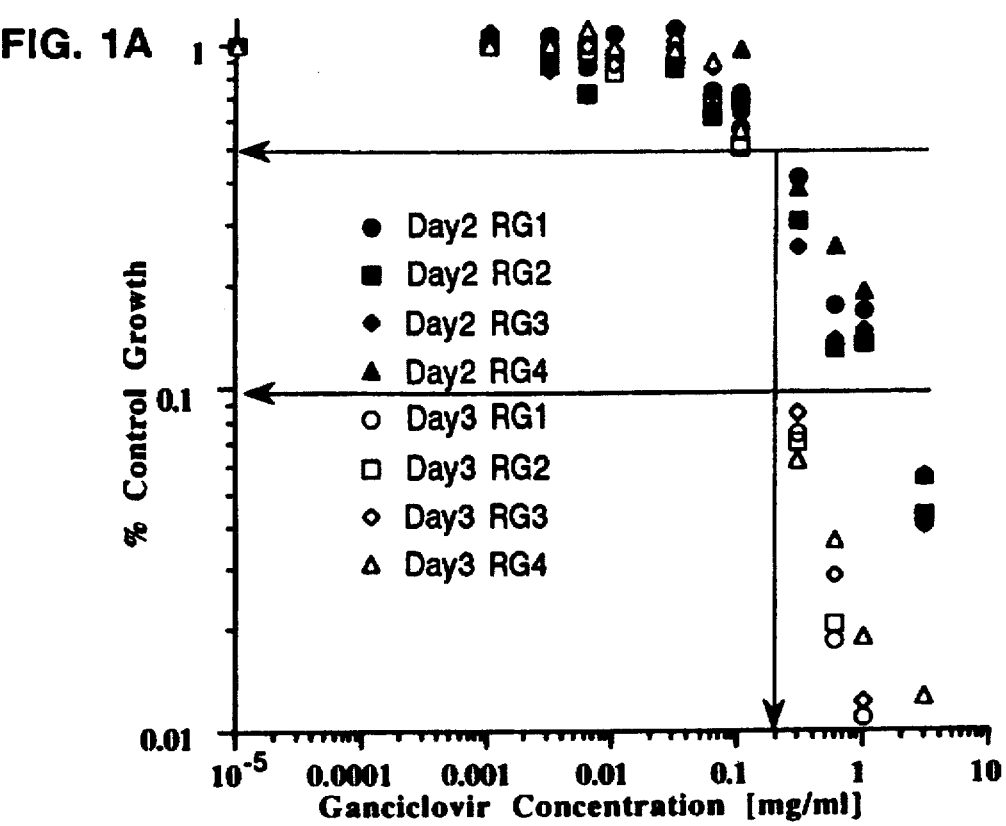
FIG. 1 shows the sensitivity profiles of different cell lines growing in ganciclovir™ containing media. A) naive RG2 cells; B) bulk culture of transduced RG2TK+ cells; and two "high-sensitivity" clones (#7 and #16) and two "low-sensitivity" clones (#32 and #35).

The subject invention provides a method of detecting gene transfer to and expression in a target tissue of a host subject comprising:
(a) administering to the host subject a transfer vector containing a marker gene not naturally present in the host and nontoxic to the host, wherein the transfer vector transfects cells of the target tissue, under conditions such that the marker gene is expressed in transfected cells of the target tissue, thereby generating a marker gene product;

(b) administering to the host subject a labelled marker substrate which is not metabolized by non-transfected cells, under conditions such that the marker substrate is metabolized by the marker gene product of step (a) to produce a labelled marker metabolite which is substantially retained in the transfected cells throughout a time-period sufficient for imaging the labelled marker metabolite; and (c) imaging the labelled marker metabolite, thereby detecting gene transfer to and expression in the target tissue.

The subject invention also provides a method of detecting gene transfer to and expression in a target tissue of a host subject comprising:

(a) administering to the host subject a transfer vector containing a marker gene, not naturally present in the host subject and nontoxic to the host, and a therapeutic gene; wherein the transfer vector transfects cells of the target tissue under conditions such that the marker and therapeutic genes are expressed in transfected cells of the target tissue, thereby generating, respectively, a marker gene product and a therapeutic gene product;

(b) administering to the host subject a labelled marker substrate which is not metabolized by non-transfected cells, under such conditions that the marker substrate is metabolized to produce a labelled marker metabolite which accumulates and is substantially retained in the transfected cells throughout a time-period sufficient for imaging the labelled marker metabolite; and (c) imaging the labelled marker metabolite, thereby detecting gene transfer to and expression in the target tissue.

DETAILED DESCRIPTION OF THE INVENTION

The subject invention provides a method of detecting gene transfer to and expression in a target tissue of a host subject comprising:

(a) administering to the host subject a transfer vector containing a marker gene not naturally present in the host and nontoxic to the host, wherein the transfer vector transfects cells of the target tissue, under conditions such that the marker gene is expressed in transfected cells of the target tissue, thereby generating a marker gene product;

(b) administering to the host subject a labelled marker substrate which is not metabolized by non-transfected cells, under conditions such that the marker substrate is metabolized by the marker gene product of step (a) to produce a labelled marker metabolite which is substantially retained in the transfected cells throughout a time-period sufficient for imaging the labelled marker metabolite; and (c) imaging the labelled marker metabolite, thereby detecting gene transfer to and expression in the target tissue.

In one embodiment, the subject invention also provides a method further comprising waiting a time-period after step (b) sufficient to allow at least 67% of non-specific label derived from residual marker substrate not metabolized by the marker gene product to clear from the subject. In another embodiment, the subject invention provides a method further comprising waiting a time-period after step (b) sufficient to allow at least 80% of non-specific label derived from residual marker substrate not metabolized by the marker gene product to clear from the subject. In yet another embodiment, the subject invention provides a method further comprising waiting a time-period after step (b) sufficient to allow at least 90% of non-specific label derived from residual marker substrate not metabolized by the marker gene product to clear from the subject.

The subject invention also provides a method as described above wherein the transfer vector transduces cells of the target tissue. In one embodiment, the subject invention provides a method wherein the marker substrate is labelled with a radioisotope suitable for imaging by positron emission tomography, gamma camera or single-photon emission computed tomography. In another embodiment, the subject invention provides a method wherein the marker substrate and marker metabolite are compounds containing a stable-isotope nuclide selected from the group consisting of $^2$H, $^{13}$C, $^{15}$N and $^{19}$F, or are paramagnetic compounds appropriate for imaging by magnetic resonance. In yet another embodiment, the subject invention provides a method wherein the labelled marker metabolite is imaged by positron emission tomography. In another embodiment, the subject invention provides a method wherein the labelled marker metabolite is imaged by gamma camera or single-photon emission computed tomography. In still another embodiment, the subject invention provides a method wherein the labelled marker metabolite is imaged by magnetic resonance imaging.

The subject invention further provides a method as described above wherein the transfer vector is nonspecific, incorporates the marker gene and suitable transcription promoter and enhancer elements, and is selected from the group consisting of a virus, a plasmid, liposomes, cells and any suitable encapsulation particle. In one embodiment, the subject invention provides a method wherein the cells are transfected with the marker gene and suitable transcription promoter and enhancer elements ex vivo prior to administration to the host subject.

The subject invention also provides a method as described above wherein the marker gene and the labelled marker substrate are selected as a self-complementary pair from the group consisting of wild-type, mutant or genetically engineered herpes simplex virus-thymidine kinase gene and a labelled 2'-fluoro-nucleoside analogue; a mutant or genetically engineered yeast glucokinase gene and a labelled 3-O-methyl glucose; and a wild-type, mutant or genetically engineered cytochrome P-450 B1 gene and a labelled imidazole substrate. In one embodiment, the subject invention provides a method wherein the labelled imidazole substrate is selected from a group consisting of 2-[$^{11}$C]-misonidazole, 2-[$^{11}$C]-metronidazole and 3-[$^{18}$F]-fluoromisonidazole. In another embodiment, the subject invention provides a method wherein the labelled 3-O-methyl glucose is selected from a group consisting of [$^{11}$C]- and [$^{18}$F]-3-O-methyl glucose. In yet another embodiment, the subject invention provides a method wherein the labelled 2'-fluoro-nucleoside analogue is selected from a group consisting of 5-[$^{123}$I]-, 5-[$_{124}$I]- and 5-[$^{131}$I]-2'-fluoro-5-iodo-1β-D-arabinofuranosyl-uracil, 5-[$^{18}$F]-2'-fluoro-5-fluoro-1-β-D-arabinofuranosyl-uracil, 2-[$^{11}$C]- and 5-([$^{11}$C]-methyl)-2'-fluoro-5-methyl-1-β-D-arabinofuranosyl-uracil, 2-[$^{11}$C]- and 5-([$^{11}$C]-ethyl)-2'-fluoro-5-ethyl-1-β-D-arabinofuranosyl-uracil, 5-(2-[$^{18}$F]-ethyl)-2'-fluoro-5-(2-fluoro-ethyl)-1-β-D-arabinofuranosyl-uracil, 5-[$^{123}$I]-, 5-[$^{124}$I]- and 5-[$^{131}$I]-2'-fluoro-5-iodovinyl-1-β-D-arabinofuranosyl-uracil, 5-[$^{123}$I]-, 5-[$^{124}$I]- and 5-[$^{131}$I]-2'- fluoro-5-iodo-1-β-D-ribofuranosyl-uracil and 5-[$^{123}$I]-, 5-[$^{124}$I]- and 5-[$^{131}$I]-2'- fluoro-5-iodovinyl-1-β-D-ribofuranosyl-uracil.

The subject invention provides a method of detecting gene transfer to and expression in a target tissue of a host subject comprising:

(a) administering to the host subject a transfer vector containing a marker gene, not naturally present in the host subject and nontoxic to the host, and a therapeutic gene; wherein the transfer vector transfects cells of the target tissue under conditions such that the marker and therapeutic genes are expressed in transfected cells of the target tissue, thereby generating, respectively, a marker gene product and a therapeutic gene product;

(b) administering to the host subject a labelled marker substrate which is not metabolized by non-transfected cells, under such conditions that the marker substrate is metabolized to produce a labelled marker metabolite which accumulates and is substantially retained in the transfected cells throughout a time-period sufficient for imaging the labelled marker metabolite; and (c) imaging the labelled marker metabolite, thereby detecting gene transfer to and expression in the target tissue. In one embodiment, the subject invention provides a method further comprising waiting a time-period after step (b) sufficient to allow at least 67% of non-specific label substantially derived from residual marker substrate not metabolized by the marker gene product to clear from the subject. In another embodiment, the subject invention provides a method further comprising waiting a time-period after step (b) sufficient to allow at least 80% of non-specific label substantially derived from residual marker substrate not metabolized by the marker gene product to clear from the subject. In yet another embodiment, the subject invention provides a method further comprising waiting a time-period after step (b) sufficient to allow at least 90% of non-specific label substantially derived from residual marker substrate not metabolized by the marker gene product to clear from the subject.

The subject invention also provides a method as described above wherein the transfer vector transduces cells of the target tissue.

The subject invention further provides a method as described above wherein step (b) further comprises administering to the host subject a therapeutic drug which is a substrate for the therapeutic gene product under conditions such that the therapeutic gene product reacts with the therapeutic drug and results in a therapeutic effect. In one embodiment, the subject invention provides a method wherein the marker substrate is labelled with a radioisotope appropriate for imaging by positron emission tomography, gamma camera or single-photon emission computed tomography. In another embodiment, the subject invention provides a method wherein the marker substrate and marker metabolite are compounds containing a stable-isotope nuclide selected from the group consisting of $^2$H, $^{13}$C, $^{15}$N and $^{19}$F, or are paramagnetic compounds appropriate for imaging by magnetic resonance.

The subject invention also provides a method as described above wherein the labelled marker metabolite is imaged by positron emission tomography. In one embodiment, the subject invention provides a method wherein the labelled marker metabolite is imaged by gamma camera or single-photon emission computed tomography. In another embodiment, the subject invention provides a method wherein the labelled marker metabolite is imaged by magnetic resonance imaging.

The subject invention provides a method as described above wherein the transfer vector is nonspecific, incorporates the marker gene, the therapeutic gene and suitable transcription promoter and enhancer elements, and is selected from the group consisting of a virus, a plasmid, liposomes, cells and any suitable encapsulation particle. In one embodiment, the subject invention provides a method wherein the cells are transfected with the marker gene, the therapeutic gene and suitable transcription promoter and enhancer elements ex vivo prior to administration to the host subject.

The subject invention also provides a method as described above wherein the marker gene and the labelled marker substrate are selected as a self-complementary pair from the group consisting of a wild-type, mutant or genetically engineered herpes simplex virus-thymidine kinase gene and a labelled 2'-fluoro-nucleoside analogue; a mutant or genetically engineered yeast glucokinase gene and a labelled 3-O-methyl glucose; and a wild-type, mutant or genetically engineered cytochrome P-450 B1 gene and a labelled imidazole substrate. In one embodiment, the subject invention provides a method wherein the labelled imidazole substrate is selected from a group consisting of [2-$^{11}$C]-misonidazole, [2-$^{11}$C]-metronidazole and [3-$^{18}$F]-fluoromisonidazole. In another embodiment, the subject invention provides a method wherein the labelled 3-O-methyl glucose is selected from a group consisting of [$^{11}$C]- and [$^{18}$F]-3-O-methyl glucose. In yet another embodiment, the subject invention provides a method wherein the labelled 2'- fluoro-nucleoside analogue is selected from a group consisting of 5-[$^{123}$I]-, 5-[$^{124}$I]- and 5-[$^{131}$I]-2'-fluoro-5-iodo-1β-D-arabinofuranosyl-uracil, 5-[$^{18}$F]-2'-fluoro-5-fluoro-1-β-D-arabinofuranosyl-uracil, 2-[$^{11}$C]- and 5-([$^{11}$C]-methyl)-2'-fluoro-5-methyl-1-β-D-arabinofuranosyl-uracil, 2-[$^{11}$C]- and 5-([$^{11}$C]-ethyl)-2'-fluoro-5-ethyl-1-β-D-arabinofuranosyl-uracil, 5-(2-[$^{18}$F]-ethyl)-2'-fluoro-5-(2-fluoro-ethyl)-1-β-D-arabinofuranosyl-uracil, 5-[$^{123}$I]-, 5-[$^{124}$I]- and 5-[$^{131}$I]-2'-fluoro-5-iodovinyl-1-β-D-arabinofuranosyl-uracil, 5-[$^{123}$I]-, 5-[$^{124}$I]- and 5-[$^{131}$I]-2'-fluoro-5-iodo-1-β-D-ribofuranosyl-uracil and 5-[$^{123}$I]-, 5-[$^{124}$I]- and 5-[$^{131}$I]-2'-fluoro-5-iodovinyl-1-β-D-ribofuranosyl-uracil.

The subject invention also provides a method as described above wherein the marker gene and the therapeutic gene are the same. In one embodiment, the subject invention provides a method wherein the marker substrate is the same as the therapeutic drug.

In a gene therapy protocol for treating a disease in a host subject, the subject invention also provides a method as described above wherein the marker gene (the therapeutic gene) is herpes simplex virus-thymidine kinase gene; wherein the marker substrate and the therapeutic drug are a 2'-fluoro-nucleoside analogue, labelled and unlabelled, respectively; wherein the labelled and unlabelled 2'-fluoro-nucleoside analogue is administered at the same or different times in relative amounts effective to generate optimal images and to treat the disease. In one embodiment, the subject invention provides a method wherein the labelled 2'-fluoro-nucleoside analogue is selected from a group consisting of 5-[$^{123}$I]-, 5-[$^{124}$I]- and 5-[$^{131}$I]-2'-fluoro-5-iodo-1β-D-arabinofuranosyl-uridine, 5-[$^{18}$F]-2'-fluoro-5-fluoro-1-β-D-arabinofuranosyl-uracil, 2-[$^{11}$C]- and 5-([$^{11}$C]-methyl)-2'-fluoro-5-methyl-1-β-D-arabinofuranosyl-uracil, 2-[$^{11}$C]- and 5-([$^{11}$C]-ethyl)-2'-fluoro-5-ethyl-1-β-D-arabinofuranosyl-uracil, 5-(2-[$^{18}$F]-ethyl)-2'-fluoro-5-(2-fluoro-ethyl)-1-β-D-arabinofuranosyl-uracil, 5-[$^{123}$I]-, 5-[$^{124}$I]- and 5-[$^{131}$I]-2'-fluoro-5-iodovinyl-1-β-D- arabinofuranosyl-uracil, 5-[$^{123}$I]-, 5-[$^{124}$I]- and 5-[$^{131}$I]-2'-fluoro-5-iodo-1-β-D-ribofuranosyl-uracil and 5-[$^{123}$I ]-, 5-[$^{124}$I]- and 5-[$^{131}$I]-2'-fluoro-5-iodovinyl-1-β-D-ribofuranosyl-uracil. In another embodiment, the subject invention provides a method wherein the marker substrate and the therapeutic drug are different.

In a gene therapy protocol for treating a disease in a host subject, the subject invention provides a method as described above wherein the marker gene (the therapeutic gene) is a wild-type, mutant or genetically engineered herpes simplex virus-thymidine kinase gene; wherein the marker substrate is a labelled 2'- fluoro-nucleoside analogue; wherein the therapeutic drug is ganciclovir™ or acyclovir™; and wherein the marker substrate and the therapeutic drug are administered at the same or different times in relative amounts effective to generate optimal images and to treat the disease. In another embodiment, the subject invention provides a method wherein the labelled 2'- fluoro-nucleoside analogue is selected from a group consisting of 5-[$^{123}$I]-, 5-[$^{124}$I]- and 5-[$^{131}$I]-2'-fluoro-5-iodo-1β-D-arabinofuranosyl-uracil, 5-[$^{18}$F]-2'-fluoro-5-fluoro-1-β-D-arabinofuranosyl-uracil, 2-[$^{11}$C]- and 5-([$^{11}$C]-methyl)-2'-fluoro-5-methyl-1-β-D-arabinofuranosyl-uracil, 2-[$^{11}$C]- and 5-([$^{11}$C]-ethyl)-2'-fluoro-5-ethyl-1-β-D-arabinofuranosyl-uracil, 5-(2-[$^{18}$F]-ethyl)-2'-fluoro-5-(2-fluoro-ethyl)-1-β-D-arabinofuranosyl-uracil, 5-[$^{123}$I]-, 5-[$^{124}$I]- and 5-[$^{131}$I]-2'-fluoro-5-iodovinyl-1-β-D-arabinofuranosyl-uracil, 5-[$^{123}$I]-, 5-[$^{124}$I]- and 5-[$^{131}$I]-2'-fluoro-5-iodo-1-β-D-ribofuranosyl-uracil and 5-[$^{123}$I]-, 5-[$^{124}$I]- and 5-[$^{131}$I]-2'-fluoro-5-iodovinyl-1-β-D-ribofuranosyl-uracil.

The subject invention further provides a method as described above wherein the marker gene and the therapeutic gene are different.

In a gene therapy protocol for treating a disease in a host subject, the subject invention provides a method as described above wherein the marker gene and the labelled marker substrate are selected as a self-complementary pair from the group consisting of a wild-type, mutant or genetically engineered herpes simplex virus-thymidine kinase gene and a labelled 2'-fluoro-nucleoside analogue; a mutant or genetically engineered yeast glucokinase gene and a labelled 3-O-methyl glucose; and a wild-type, mutant or genetically engineered cytochrome P-450 B1 gene and a labelled imidazole substrate; the therapeutic gene is selected from a group consisting of IL-2 gene, IL-4 gene, gamma-interferon gene, adenosine deaminase gene and neural growth factor gene; and wherein the therapeutic gene product is expressed in an amount effective to treat the disease. In one embodiment, the subject invention provides a method wherein the labelled 2'-fluoro-nucleoside analogue is selected from a group consisting of 5-[$^{123}$I]-, 5-[$^{124}$I]- and 5-[$^{131}$I]-2'-fluoro-5-iodo-1β-D-arabinofuranosyl-uracil, 5-[$^{18}$F]-2'-fluoro-5-fluoro-1-β-D-arabinofuranosyl-uracil, 2-[$^{11}$C]- and 5-([$^{11}$C]-methyl)-2'-fluoro-5-methyl-1-β-D-arabinofuranosyl-uracil, 2-[$^{11}$C]- and 5-([$^{11}$C]-ethyl)-2'-fluoro-5-ethyl-1-β-D-arabinofuranosyl-uracil, 5-(2-[$^{18}$F]-ethyl)-2'-fluoro-5-(2-fluoro-ethyl)-1-β-D-arabinofuranosyl-uracil, 5-[$^{123}$I]-, 5-[$^{124}$I]- and 5-[$^{131}$I]-2'-fluoro-5-iodovinyl-1-β-D-arabinofuranosyl-uracil, 5-[$^{123}$I]-, 5-[$^{124}$I]- and 5-[$^{131}$I]-2'-fluoro-5-iodo-1-β-D-ribofuranosyl-uracil and 5-[$^{123}$I]-, 5-[$^{124}$I]- and 5-[$^{131}$I]-2'-fluoro-5-iodovinyl-1-β-D-ribofuranosyl-uracil.

The subject invention also provides a method as described above wherein the marker substrate and the therapeutic drug are different.

In a gene therapy protocol for treating a disease in a host subject, the subject invention provides a method as described above wherein the marker gene and the labelled marker substrate are selected as a self-complementary pair from the group consisting of a wild-type, mutant or genetically engineered herpes simplex virus-thymidine kinase gene and a labelled 2'-fluoro-nucleoside analogue; a mutant or genetically engineered yeast glucokinase gene and a labelled 3-O-methyl glucose; wherein the therapeutic gene and the therapeutic drug are selected as a self-complementary pair from a group consisting of cytosine deaminase gene and 5-fluorocytosine, E. coli gpt gene and 6-thioxanthine, E. coli DeoD gene and 6-methylpurine-2'-deoxyribonucleoside, and cytochrome P450 2B1 gene and cyclophosphamide; and wherein the marker substrate and the therapeutic drug are administered at the same or different times in relative amounts effective to generate optimal images and to treat the disease. In one embodiment, the subject invention provides a method wherein the labelled 2'-fluoro-nucleoside analogue is selected from a group consisting of 5-[$^{123}$I]-, 5-[$^{124}$I]- and 5-[$^{131}$I]-2'-fluoro-5-iodo-1β-D-arabinofuranosyl-uracil, 5-[$^{18}$F]-2'-fluoro-5-fluoro-1-β-D-arabinofuranosyl-uracil, 2-[$^{11}$C]- and 5-([$^{11}$C]-methyl)-2'-fluoro-5-methyl-1-β-D-arabinofuranosyl-uracil, 2-[$^{11}$C]- and 5-([$^{11}$C]-ethyl)-2'-fluoro-5-ethyl-1-β-D-arabinofuranosyl-uracil, 5-(2-[$^{18}$F]-ethyl)-2'-fluoro-5-(2-fluoro-ethyl)-1-β-D-arabinofuranosyl-uracil, 5-[$^{123}$I]-, 5-[$^{124}$I]- and 5-[$^{131}$I]-2'-fluoro-5-iodovinyl-1-β-D-arabinofuranosyl-uracil, 5-[$^{123}$I]-, 5-[$^{124}$I]- and 5-[$^{131}$I]-2'-fluoro-5-iodo-1-β-D-ribofuranosyl-uracil and 5-[$^{123}$I]-, 5-[$^{124}$I]- and 5-[$^{131}$I]-2'-fluoro-5-iodovinyl-1-β-D-ribofuranosyl-uracil.

The subject invention encompasses detection of gene transfer to and expression in a variety of tissues in a host subject, which include, but are not restricted to, the brain, liver, heart, kidney, spleen, intestine, epidermis, lung, eye, blood vessels and arteries, and nerves. The term "host subject" as used herein is intended to encompass any warm- or cold-blooded animal, including primarily, but not restricted to, humans.

When practicing the subject invention in conjunction with gene therapy, it is possible to monitor gene transfer of a therapeutic gene to, and expression thereof in, a host subject suffering from a variety of diseases, including but not limited to, sarcomas, carcinomas, melanomas, gene deficiencies and abnormalities, such as adenosine deaminase deficiency, as well as cystic fibrosis, hypercholesterolemia, lysosomal storage disease, and diabetes.

Conditions for administering to the host subject both a transfer vector and a marker substrate are determined for each host subject using methods generally known and accepted in the medical art. Various modes of administration include, but are not restricted to, direct injection (e.g., intratumoral, intraarterial, intravenous, subcutaneous, and intramuscular), surgical implantation, inhalation, and hypervelocity injection/bombardment. Optimal amounts of marker genes and labelled marker substrates, and dosages of therapeutic genes and/or drugs to be administered may be determined by those skilled in the art, and will vary with the particular complementary pair of marker gene/substrate and/or therapeutic gene/drug in use, the strength of the preparation, the mode of administration, and/or the advancement of the disease condition being monitored or treated. Three factors based determine whether additional vector, marker substrate or therapeutic drug should be administered, namely, level of expression of the vector, stability of transduction, and efficacy of treatment. The level of marker gene expression and the stability of transduction can be assessed by qualitative and quantitative imaging following administration of marker substrate. If treatment efficacy is low, transduction is unstable, or expression is inefficient, then administration of the vector, marker substrate or drug may be repeated. In the current art, about $10^4$–$10^{11}$ vector particles bearing the marker or therapeutic gene are administered, usually about $10^6$ or higher amounts being preferred. Additional factors depending on the particular patient being monitored and/or treated will result in a need to adjust amounts/dosages, including patient age, weight, gender, diet, and time of administration.

The following Experimental Details are set forth to aid in an understanding of the invention, and are not intended, and should not be construed, to limit in any way the invention set forth in the claims which follow thereafter.

EXPERIMENTAL DETAILS

General

Source of materials. The RG2 glioma cell line was originally derived from an ethylnitrosourea (ENU)-induced rat glioma [Ko, L., Koestner, A., and Wechsler, W., Acta Neuropathol. (Berl.), 84: 529–41, 1980]. The gp-STK-A2 producer cell line produces the recombinant STK retrovirus containing the HSV1-thymidine kinase gene, [Moolten, F. L. and Wells, J. M., J. Natl. Cancer Inst. 82 (4): 297–300, 1990] The STK retrovirus also contains a NeoR gene which encodes resistance to the neomycin analogue Geneticin™ disulfate and the SV40 early region promoter and enhancer. [Moolten, F. L. and Wells, J. M., J. Natl. Cancer Inst. 82 (4): 297–300, 1990]

Abbreviations

FCS fetal calf serum

MEM minimal essential medium

NEAA non-essential amino acids

PS permeability surface (area)

QAR quantitative autoradiography

TCA trichloroacetic acid

EXAMPLE 1

Transduction of the HSV1-TK gene into RG2 cells. The STK retrovirus was obtained from filtered (0.1 μm) supernatants of gp-STK-A2 producer cell line cultures grown from a 50% confluent monolayer over 24 hours in Dulbecco's high-glucose medium with 10% bovine serum. Transduction of RG2 cells was accomplished by exposing the cell monolayer to the filtrate for 8 hours in the presence of Polybrene™ (8 μg/ml). Following a 24 hour incubation in standard medium, a selection medium containing Geneticin™ disulfate (800 μg/ml) was used to eliminate cells not expressing the neomycin resistance gene. The selection medium was changed daily to remove dead cells. After 7 days, a bulk culture of transduced RG2 cells (RG2TK+) was harvested for further propogation.

EXAMPLE 2

Cell culture procedures and isolation of HSV1-TK expressing clones. All the cell cultures were grown in monolayers on Costar™ 162 cm² tissue culture flasks with 0.2 μm ventilated filter caps at 37° C. in a 5% $CO_2$ humidified incubator. The RG2TK+ (multiple clone) cell line and individual RG2TK+ clones were grown in minimum essential medium with nonessential amino acids (MEM+NEAA) supplemented with 10% heat inactivated FCS and Geneticin™ disulfate (250 μg/ml). The non-transduced RG2 cell line cell was maintained in the same manner, but without Geneticin™ disulfate.

A ring-cloning procedure was used to obtain single clones (total of 220 clones) of HSV-TK gene-transduced cells. The individual clones were seeded into the small Petri dishes (50×10 mm) in the Geneticin™ disulfate (800 μg/ml) selection media, and expanded to the T75 (Costar™ 75 cm²) tissue culture flasks. After 5 passages bulk of RG2TK+ cells and individual clones were harvested, frozen in a freezing media, and stored in liquid nitrogen until further use.

Cell suspensions were prepared for in vitro studies of sensitivity to ganciclovir™ and for accumulation studies of radiolabelled nucleosides. The medium was removed from the culture flasks, rinsed with 0.05% trypsin-EDTA to neutralize the remaining FCS, and the monolayers were then incubated with fresh 0.05% trypsin-EDTA for 5 minutes at 37° C. The cells were collected and washed twice in serum-free medium, resuspended and seeded in Costar™ 96-well plates (100 cells/well) or Fisher 150×25 mm Petri dishes) at 5000 cells/Petri dish). They were allowed to grow until they become 50 to 90% confluent.

EXAMPLE 3

Independent assays of HSV1-tk gene expression in different RG2TK cell lines. Two independent assays for HSV1-tk gene expression were performed in several different RG2TK cell lines: a) sensitivity to the antiviral drug ganciclovir™, and b) measurements of HSV-TK mRNA. Ganciclovir™ sensitivity is a functional assay for the presence of HSV1-TK (cells that do not express HSV1-TK have a very high $ED_{50}$). HSV-TK mRNA expression is a specific, but indirect measure of HSV1-TK. Both measures were correlated with "marker substrate" accumulation in different RG2TK cell lines in culture (see FIG. 7). Similarly, both measures are correlated with "marker substrate" accumulation in i.c. and s.c. tumors in animals; tumors are produced by the same cell lines studied in tissue culture.

EXAMPLE 4

Sensitivity to ganciclovir and selection of "high" and "low" sensitivity clones. Expression of HSV1 thymidine kinase in the RG2-TK+ and RG2 cell lines was tested by sensitivity to ganciclovir™ in culture. Following one day of growth, the culture medium of RG2TK+ and RG2 cells in Costar™ 96-well plates was replaced with ganciclovir™-containing medium (Cytovene™; Syntax Laboratories, Inc.; Palo Alto, Calif.) in the following concentrations: 3, 1, 0.6, 0.3, 0.1, 0.06, 0.03, 0.01, 0,006, 0.003, 0.001, 0.0006, 0.0003, 0.0001, 0.00006 mg/ml and ganciclovir™-free control media. The ganciclovir™-containing and control incubation media were changed daily. Methyl-[³H]-thymidine (TdR) (64.7 Ci/mmol; Moravek Biochemicals Inc., Brea, Calif.) accumulation studies were performed in quadruplicate on the third and fourth day to measure cell division. The cells in each well were exposed to methyl-[³H]-thymidine for 4 hours at a concentration of 0.5 uCi/well, collected on glass filter paper (0.2 um) with a cell harvestor (Cambridge Technologies, Inc.), and prepared for counting (see below) to determine dpm/well. Radioactivity measured in each ganciclovir™-containing well was expressed as a percent of control (ganciclovir™-free) activity.

Figure 1B:
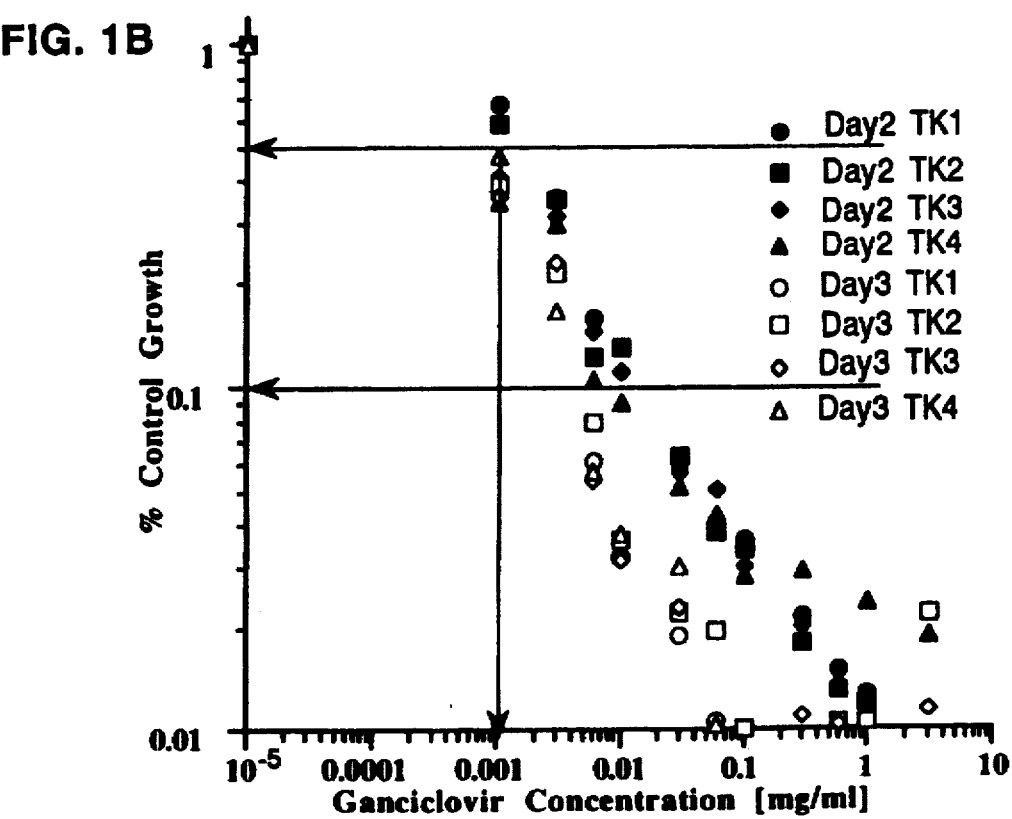

The sensitivity profiles for RG2 cells in quadruplicate following 2 and 3 days of ganciclovir™ exposure are shown in FIG. 1A. Similar profiles for bulk RG2TK+ cells are shown in FIG. 1B. The ganciclovir™ $ED_{50}$ dose was 0.2 mg/cc for wild-type RG2 cells and 0.001 mg/cc for RG2TK+ cells. Bulk RG2TK+ cells are approximately 200-fold more sensitive to ganciclovir™ than RG2 cells. This indicates that the bulk culture of RG2TK+ cells is producing HSV1 thymidine kinase.

Figure 1C:
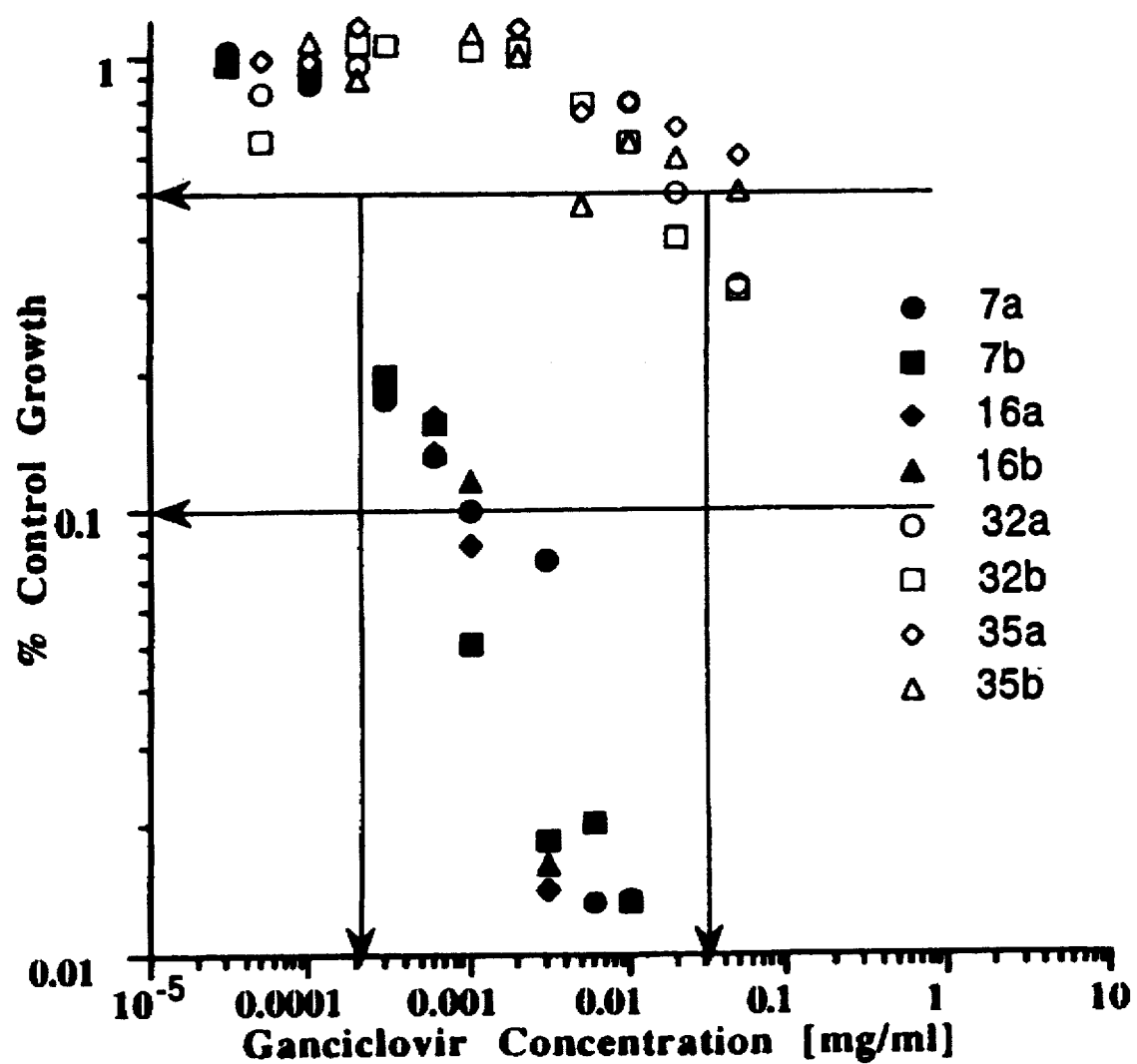

The ganciclovir™ sensitivity assay was performed on 42 of 220 separate RG2TK+ clones that were isolated from the bulk culture of transfected RG2TK+ cells. The profiles of two "high" sensitivity (#7 and #16) clones and two "low" sensitivity (#32 and #35) clones are shown in FIG. 1C. The ganciclovir™ $ED_{50}$ dose was approximately 0.0002 mg/cc for the "high" sensitivity RG2TK+ clones and approximately 0.03 mg/cc for the "low" sensitivity RG2TK+ clones. The "high" sensitivity RG2TK+ clones were 5-fold more sensitive to ganciclovir™ compared to the bulk culture of transfected RG2TK+ cells, whereas the "low" sensitivity clones were roughly 30-fold less sensitive.

EXAMPLE 5

Expression of HSV1-TK mRNA in transduced cell lines. Northern blot analysis of HSV-TK+ expression in the wild-type RG2 and RG2TK+ cell lines was performed. Total RNA was extracted by the single-step guanidinium method followed by electrophoresis under denaturing conditions in a 1% agarose-formaldehyde gel loading 20 µg of RNA sample per lane. Transfer of the RNA to Hybond-N+™ membranes (Amersham Corp., Ill.) was performed over 4 hours in 0.05M NaOH. Hybridization was performed with a $^{32}$P-labelled BglII-NcoI fragment of HSV-TK cDNA probe overnight at 42° C. in 50% formamide, 10% polyethyleneglycol 6000, 3.5% sodium dodecyl sulfate (SDS), 150 mM sodium phosphate buffer, pH 6.8, 250 mM NaCl, 1 mM ethylenediaminetetraacetic acid (EDTA), 2× Denhardt's solution. The blots were washed for 15 minutes in 2× SSc, 5 mM sodium phosphate buffer, 1 % SDS, 0.02% tetrasodium pyrophosphate at room temperature, followed by two washes at 70° C. for 30 minutes each in the same solution, but containing 0.1× SSC. A final wash without SDS was performed for 5 minutes and the blots were exposed to Hyperfilm-MP™ (Amersham Corp., Ill.) with an intensifying screen for 1–3 days at –80° C. Thereafter, the blot was stripped and re-probed for U3 (probe recognizing MoMLV-specific RNA transcripts) [Gansbacher, B., Zier, K., Cronin, K., Hantzopolous, B., Bouchard, B., Houghton, A., Gilboa, E., and Golde, D., Blood, 80: 2817–25, 1992] or beta-actin. The integrated optical density (IOD) values of HSV1-tk mRNA were measured from the autoradiograms and normalized to the IOD values of 28S RNA (ethidium bromide stain) in corresponding lanes.

Northern blot analysis of the wild-type RG2 and RG2TK+ cell lines confirmed high level of expression of HSV-TK mRNA in the bulk RG2TK+ cell line and the absence of HSV-TK mRNA in naive RG2 cells (FIG. 2A). A similar northern blot analysis of the high and low ganciclovir™ sensitivity clones demonstrated substantially higher HSV-TK mRNA expression in the high-sensitivity clone (#16) compared to that in the low-sensitivity clone (#32) (FIG. 2B). The low sensitivity to ganciclovir™ of clone #32 can be explained not only by the lower levels of HSV-TK expression (FIG. 2B), but also by presence of a spliced form of HSV-TK mRNA. This spliced form of HSV-TK mRNA is visualized as an additional band below HSV-TK mRNA (FIG. 2B). The retroviral origin of this band was confirmed by re-hybridization of the blot with the U3 probe (FIG. 2C).

Figure 3A:
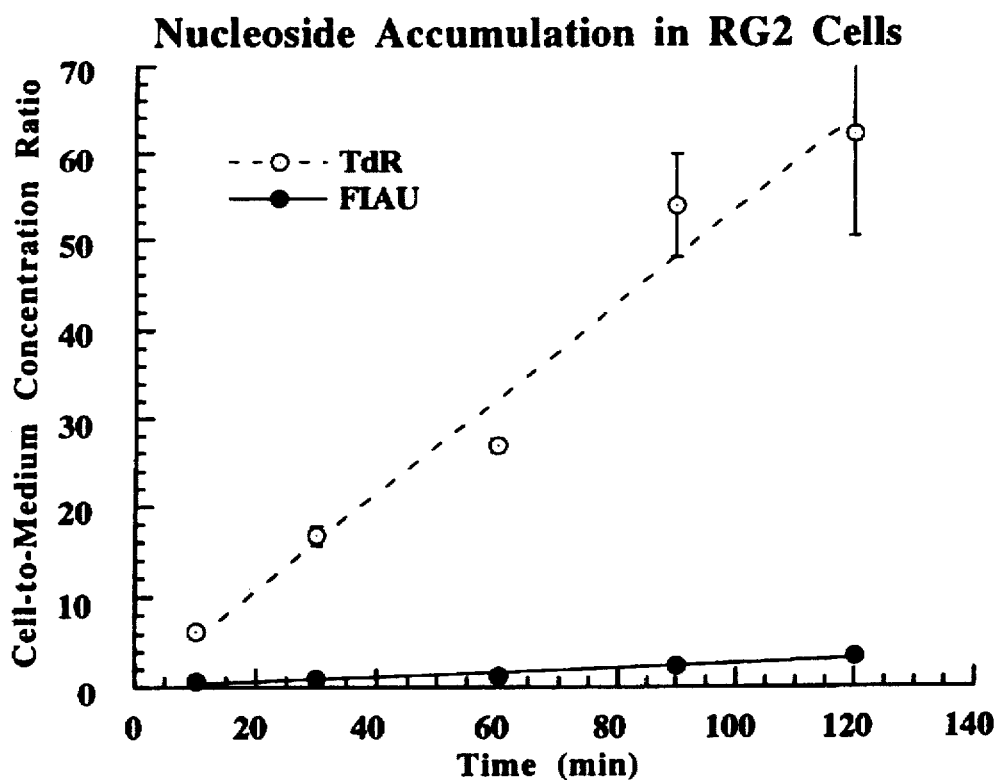
FIG. 3 shows a time course of TdR and FIAU accumulation in nontransformed RG2 cells and transformed RG2TK+ cells.
Figure 3B:
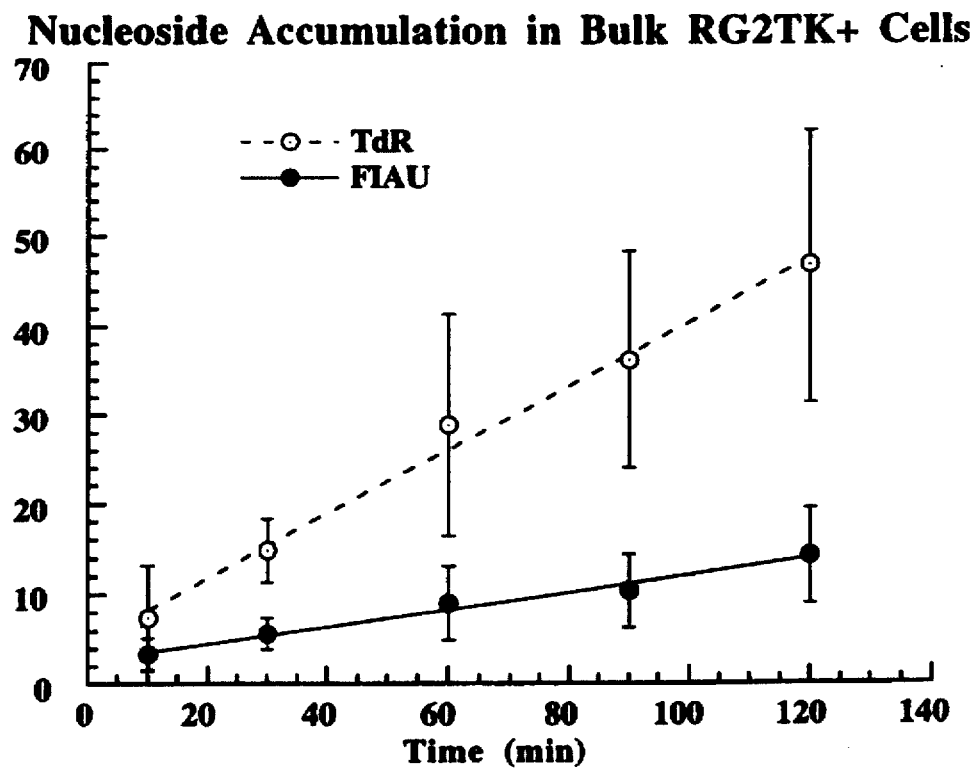

Source of radiolabelled "marker substrates". The source of 2-[$^{14}$C]-2'-fluoro-5-iodo-1-β-D-arabino-furanosyl-uracil (FIAU) (56 mCi/mmol), 6-[$^3$H]-5-iododeoxyuridine (IUdR) (14.7 Ci/mmol), 8-[$^3$H]-ganciclovir™ (17.9 Ci/mmol), and 2-[$^{14}$C]-thymidine (TdR) (54 mCi/mmol) was Moravek Biochemicals, Inc. Radiochemical purity of each compound was checked by high performance liquid chromatography (HPLC), and found to be >98%. Double-label studies were performed and all uptake values were normalized to that of TdR in order to control for differences in cell proliferation in the different experiments. The activity of 2-[$^{14}$C]-FIAU and methyl-[$^3$H]-TdR was 0.01 and 0.2 µCi/ml, respectively (FIG. 3 and 4A); the activity of 8-[$^3$H]-ganciclovir™ and 2-[$^{14}$C]-TdR was 0.5 and 0.02 µCi/ml, respectively (FIG. 4B); and the activity of 6-[$^3$H]-IUdR and [2-$^{14}$C]-TdR was 0.2 and 0.01 µCi/ml, respectively (FIG. 4C). No carrier-added 5-[$^{123}$I]-deoxyuridine (IUdR) was prepared by reacting 2-deoxyuridine (UdR) with carrier-free $^{123}$I-labelled sodium iodide in an iodogen coated reaction vial. The use of pre-conditioned Waters SepPak™ $C_{18}$ cartridges resulted in analytically pure IUdR (99±0.5%), at a yield of 73.8±8.3%.

FIG. 4 shows a comparison of the cell-to-medium accumulation ratios in transduced RG2TK+ and naive RG2 cells for different nucleoside analogues: (A) 2-[$^{14}$C]-FIAU; (B) 8-[$^3$H]-Ganciclovir™; (C) 6[$^3$H]-IUdR. The slope of each plot represents nucleoside accumulation normalized to that of TdR.

EXAMPLE 6

Comparison of "marker substrates" for identifying HSV1-tk gene expression in tissue culture. Three potential "marker substrates" for the enzyme HSV1-TK were selected (FIAU, IUdR, and ganciclovir™), and compared by measuring their accumulation in RG2TK+ transduced cells and in RG2 wild-type cells. Each of these substrates were developed for or used as an anti-viral agent; they are phosphorylated by HSV1-TK and can be radiolabelled for noninvasive imaging. Iododeoxyuridine (IUdR) incorporates into the DNA of dividing cells (substitutes for thymidine); it was initially used as an anti-vital agent and more recently it has been used to image tumor proliferation. Ganciclovir™ was developed as a more effective anti-vital agent and has recently been used in combination with HSV1-tk in clinical gene therapy protocols. 2'-Fluoro-5-iodo-1-β-D-arabinofuranosyl-uracil (FIAU) was also developed as an anti-viral agent; it is resistant to metabolic degradation (hydrolysis by thymidine phosphorylase) which makes it an ideal radiotracer.

Three different lines of RG2TK+ transduced cells were studied, including the "bulk" transfected cell line and two individual clones exhibiting "high" sensitivity (clone #16) and "low" sensitivity (clone #32) to ganciclovir™. Wild-type (nontransduced) RG2 cells were studied as a reference control. The incubation medium of the RG2TK+ and RG2 cells in 150×25 mm Petri dishes was replaced with 15 ml of medium containing various combinations of tracer radiolabelled "marker substrate" and radiolabelled thymidine. The cells were harvested after various periods of incubation: 10, 30, 60, 90, 120 minutes for the FIAU and IUdR studies; and 1, 2, 4, 6, 8, 24 and 30 hours for the ganciclovir™ study. The cells were dislodged from the Petri dishes with a soft scraper, poured into 15 ml conical tubes, centrifuged and the medium aspirated. The tubes were cut to facilitate removing cells; they were blotted, placed in pre-weighed vials, weighed and prepared for counting. Samples were assayed for $^3$H- and $^{14}$C-radioactivity using a Packard B1600 Tri-Carb beta spectrometer using dual-channel and external standard splash and quench correction techniques. The medium was also counted before and following incubation. The data was expressed as a harvested cell-to-medium concentration ratio (dpm/g cells+dpm/ml medium). An example of one triplicate experiment measuring the time course of TdR and FIAU accumulation in non-transformed RG2 cells and transformed RG2TK+ cells is shown in FIG. 3.

Cell proliferation varied somewhat between experiments for both transduced RG2TK+ and non-transduced RG2 cell cultures as determined by cell counting techniqes (data not shown) and thymidine accumulation. When the proliferation of RG2TK+ and RG2 cells differed, the cultures with a lower rate of proliferation (as determined by cell counting) were always associated with a lower rate of thymidine accumulation. When cell proliferation in the cultures was similar, similar rates of thymidine accumulation were obtained in both cell lines. These results support normalization of nucleoside analogue accumulation to that of thymidine in order to account for differences in cell proliferation between experiments.

Figure 4A:
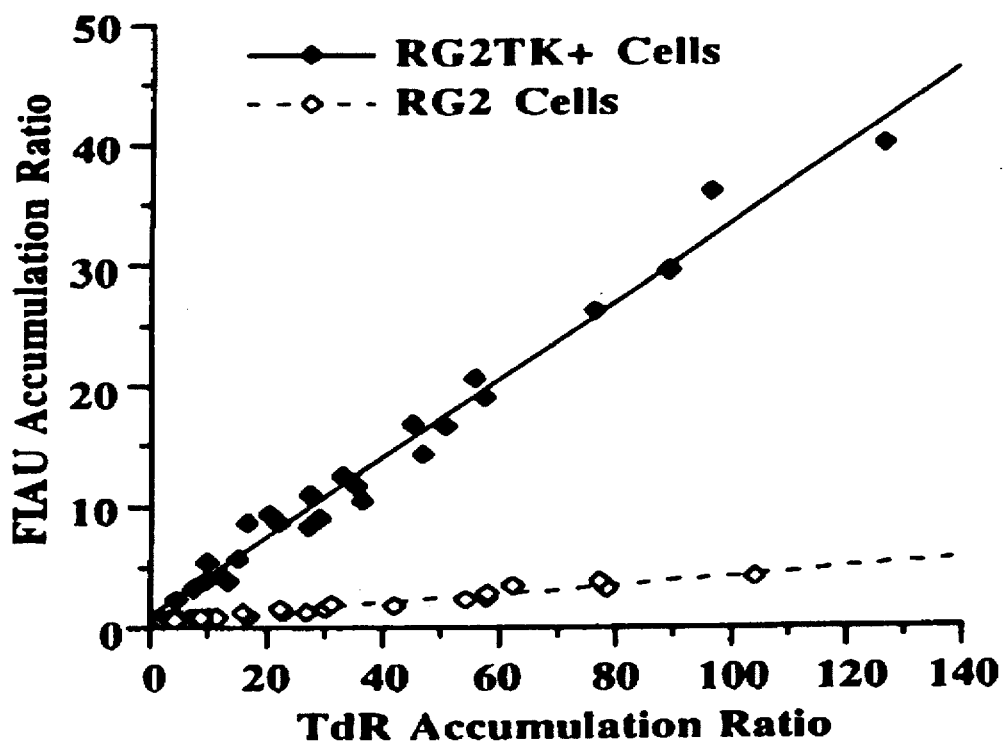
FIG. 4 shows a comparison of the cell-to-medium accumulation ratios in transduced RG2TK+ and naive RG2 cells for different nucleoside analogues. A) 2-[$^{14}$C]-FIAU; B) 8-[$^{3}$H]-Ganciclovir™; C) 6[$^{3}$H]-IUdR. The slope of each plot represents nucleoside accumulation normalized to that of TdR.
Figure 4B:
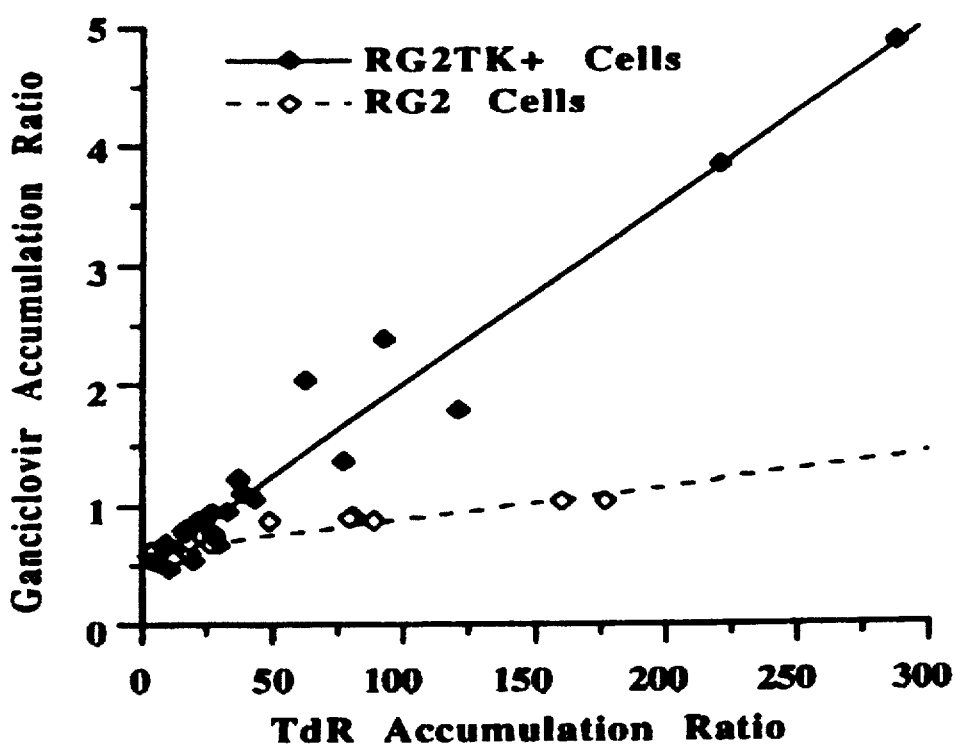
Figure 4C:
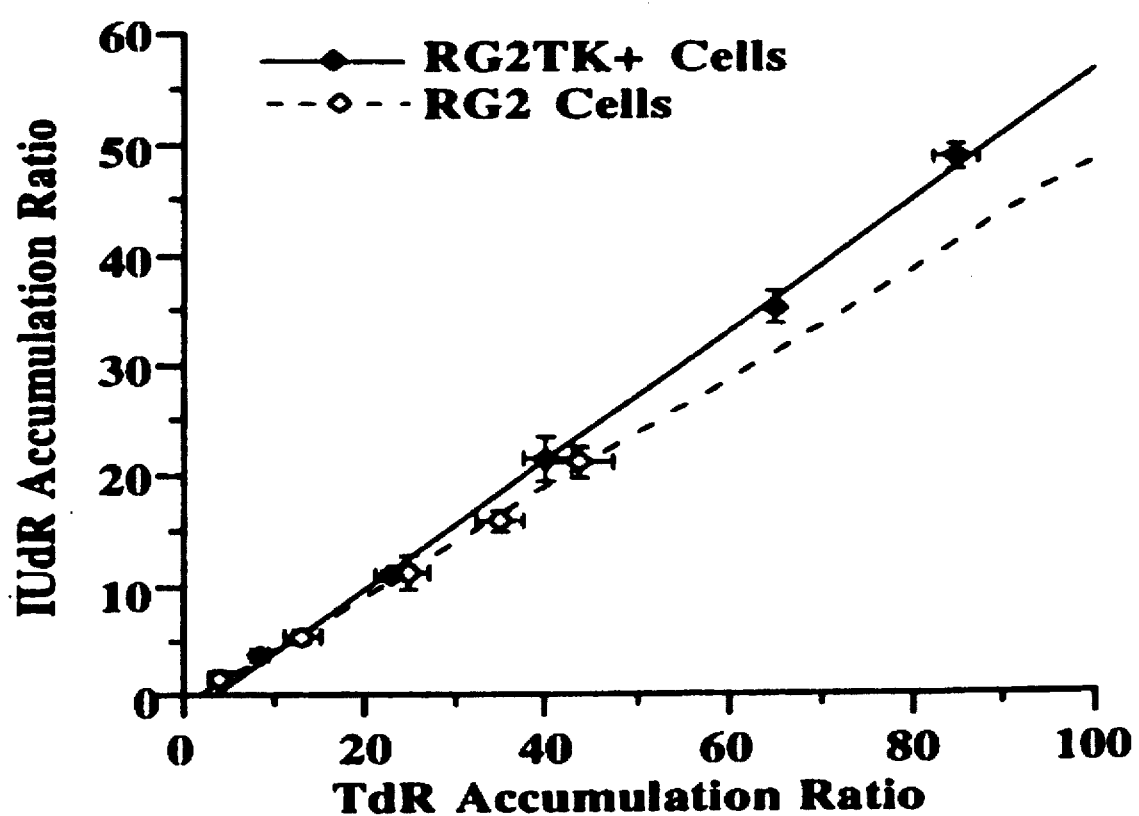
Figure 5A:
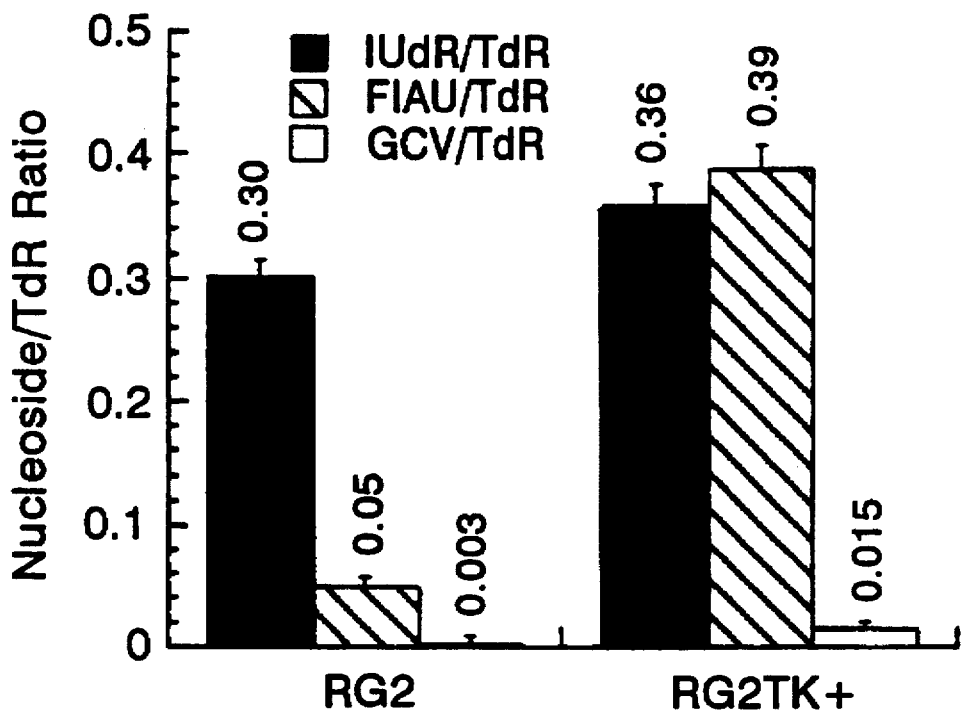
FIGS. 5A and 5B show a comparison of nucleoside analogue accumulation ratios in RG2TK+ transduced cells and naive RG2 cells. (A) Comparison of slopes plotted in FIG. 4; (B) accumulation in transduced RG2TK+ cells compared to naive RG2 cells.
Figure 5B:
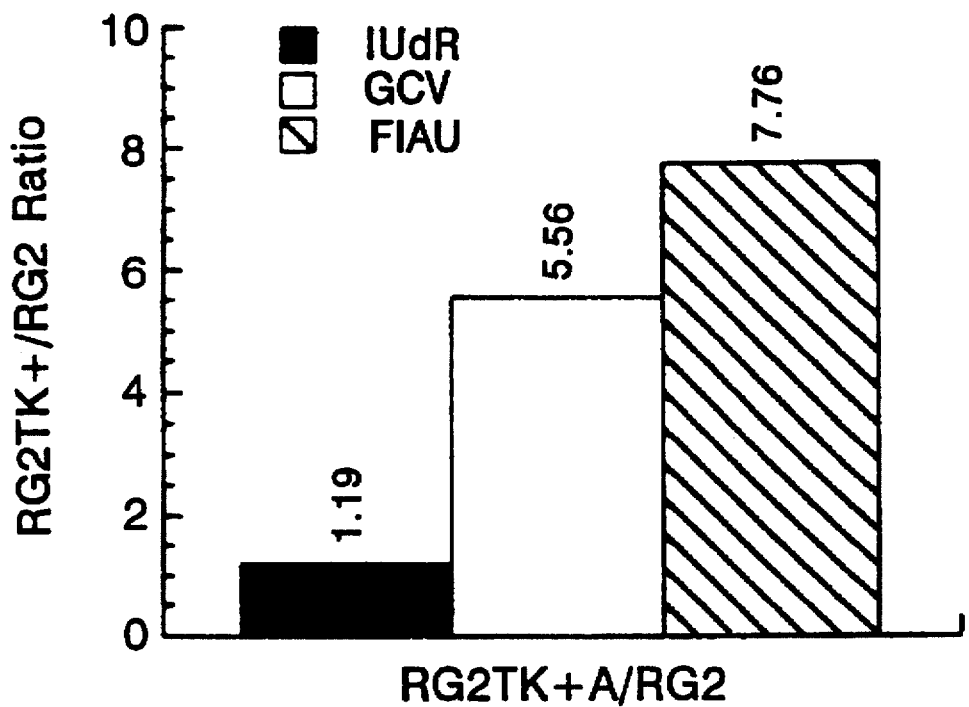

A comparison between the accumulation of the different nucleoside analogues in RG2TK+ transduced cells and non-transduced RG2 cells is shown in FIGS. 4 and 5. FIAU accumulation in bulk RG2TK+ cells was 7.8 times greater than that in wild-type RG2 cells (FIGS. 4A and 5B). Ganciclovir accumulation was 5.6 fold greater in RG2TK+ cells compared to RG2 cells (FIGS. 4B and 5B), whereas the difference was only 1.2 fold for IUdR (FIGS. 4C and 5B). The accumulation of ganciclovir™ by RG2TK+ cells was small compared to that of FIAU and IUdR (less than 5% and 3%, respectively) and may not provide a sufficient signal for imaging. Although the accumulation of IUdR by RG2TK+ cells was somewhat higher than that of FIAU in this system, the accumulation of IUdR does not distinguish between transduced RG2TK+ and non-transduced RG2 cells. This suggests that IUdR is not an effective "marker substrate" for HSV-TK gene expression in this system.

In another series of in vitro experiments the accumulation of [$^{123}$I]-IUdR was directly compared with that of 2-[$^{14}$C]-FIAU and methyl-[$^{3}$H]-TdR in RG2TK+ and RG2 cells (FIG. 6). A single 120 minute paired accumulation measurement of FIAU and IUdR by RG2TK+ and RG2 cells in 150×25 mm Petri dishes was performed as described above (FIG. 2); the activity of 5-[$^{123}$I]-IUdR, [2-$^{14}$C]-FIAU and methyl-[$^{3}$H]-TdR in the incubation medium was 0.3, 0.01 and 0.2 μCi/ml, respectively. The processing of cells and incubation medium was the same as that described above. A portion of the harvested cells was also processed for acid-insoluble (10% TCA) radioactivity. Decay corrected $^{123}$I-radioactivity was measured in a Packard AutoGamma 5550 Spectrometer. Samples were stored for 1 week to allow for $^{123}$I decay (12 half lives), and recounted afterwards in the Packard B1600 TriCarb beta spectrometer to determine $^{3}$H- and $^{14}$C-radioactivity.

Figure 6A:
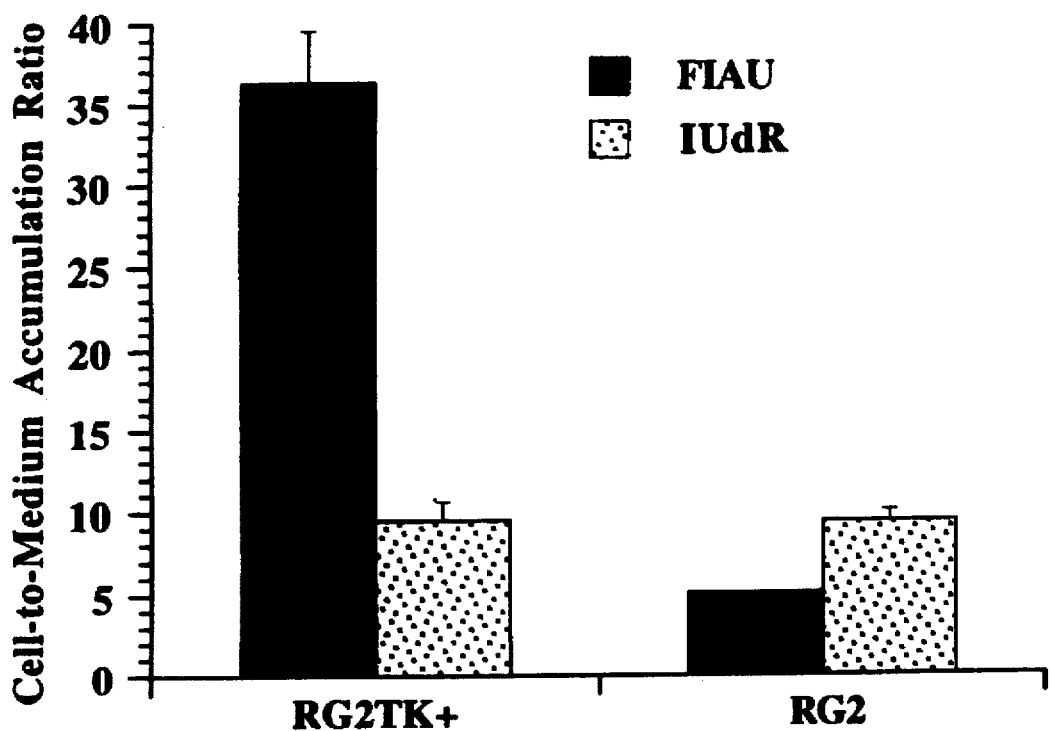
FIG. 6 shows accumulation of [$^{125}$I]-IUdr compared with that of 2-[$^{14}$C]-FIAU and methyl-[$^{3}$H]-TdR in transformed RG2TK+ and naive RG2 cells.
Figure 6B:
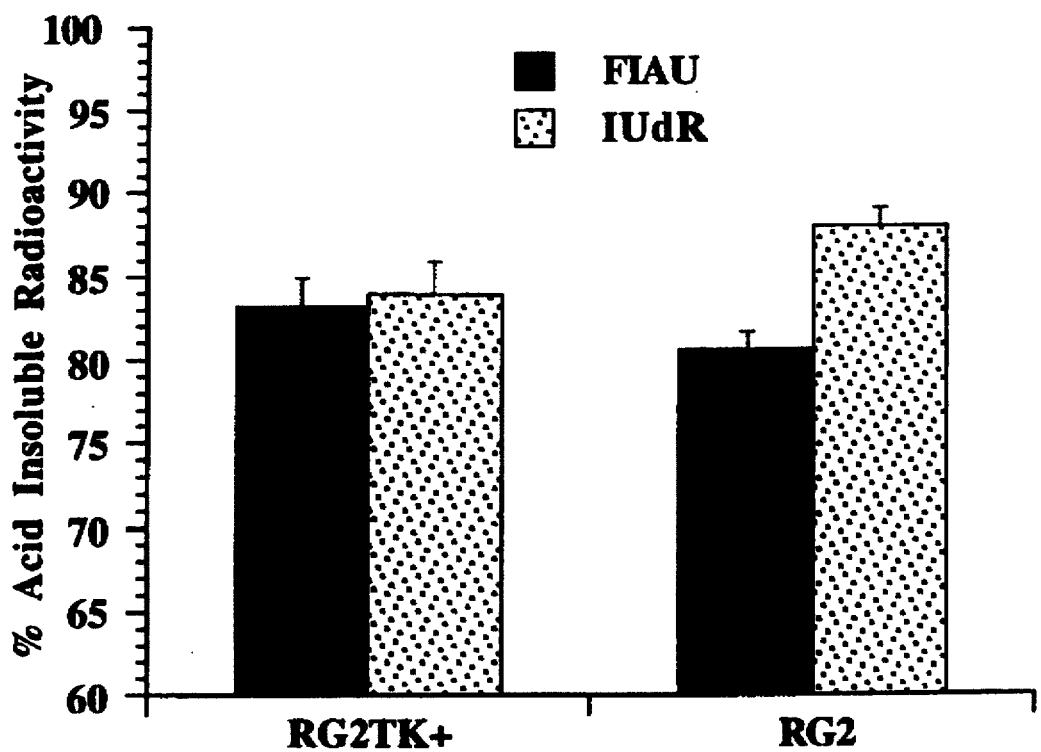

Cell proliferation was similar in both cell cultures as determined by cell counting techniques and by TdR accumulation and incorporation into DNA (data not shown). All radioactivity measurements were expressed as a percent of administered dose per gram of tissue or per unit volume of fluid as described above. The accumulation of FIAU in RG2TK+ cells was 7.2 fold greater than that in RG2 cells whereas IUdR accumulation was similar in both transduced and non-transduced cells (FIG. 6A). The acid insoluble fractions of FIAU and IUdR accumulation at 2 hours were similar, ranging between 80 and 90% of total activity, for both cell lines (FIG. 6B). This paired-comparison demonstrates the advantage of FIAU over IUdR as a "marker substrate" to distinguish between RG2TK+ transduced cells and non-transduced RG2 cells in culture.

Figure 7A:
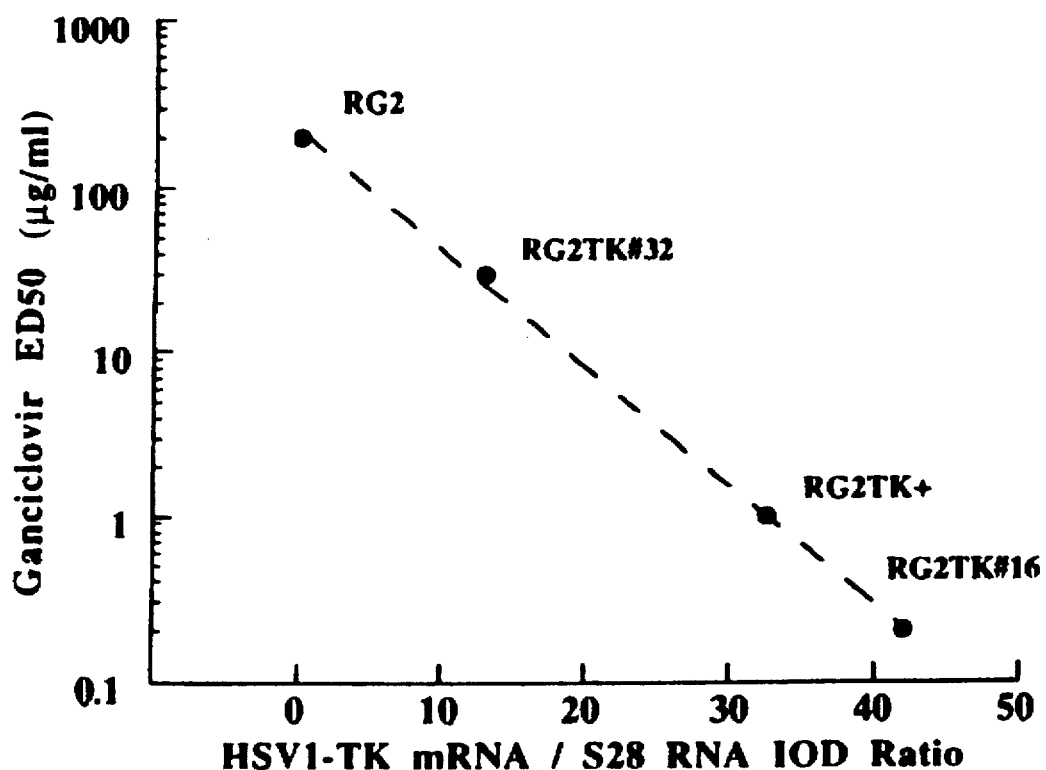
FIGS. 7A, 7B, and 7C show relationships between FIAU accumulation and HSV1-tk mRNA and sensitivity to ganciclovir™ in different RG2TK cell lines. The relationship between ganciclovir™ sensitivity ($ED_{50}$.

Relationship between HSV-TK mRNA, ganciclovir sensitivity, and FIAU Uptake. Expression of HSV1-TK mRNA in RG2TK+ cells and different RG2TK clones was compared to ganciclovir™ sensitivity (ED50) and FIAU accumulation in corresponding cell lines (FIG. 7). A highly significant inverse relationship was observed between the normalized IOD values of HSV1-TK mRNA (see FIG. 2) and ED$_{50}$ values of ganciclovir™ in corresponding cell lines (FIG. 7A), which could be described by equation:

$$ED_{50}=222*exp[-0.166*IODtk]$$

(R=0.999). Accumulation of FIAU, expressed as the FIAU/TdR uptake ratio (slope in FIG. 5), was proportional to the levels of HSV1-TK mRNA in corresponding cell lines (FIG. 7B) and could be described by the equation:

$$FIAU/TdR\ uptake\ ratio=0.0449+0.00861*IODtk$$

(R=0.999). A highly significant inverse relationship was also observed between FIAU uptake and ganciclovir™ sensitivity (FIG. 7C) and could be described by the equation: y=0.325−0.121 log(x) (R=0.999). These results indicate that the level of FIAU accumulation in different transduced cell lines correlates with the level of HSV1-tk expression as measured by HSV1-TK mRNA on Northern blot analysis and by sensitivity to ganciclovir™, a functional measure of HSV1-TK expression, in corresponding cell lines. The expected relationship between HSV1-TK mRNA and ED$_{50}$ values for ganciclovir™ was also observed.

Data analysis. To evaluate the proficiency of "marker substrates" for imaging of HSV1-tk expression, two parameters were used: 1) "sensitivity", defined as the change in substrate uptake (normalized to TdR) divided by the change in HSV1-tk expression, and 2) "selectivity", defined as "sensitivity" divided by substrate uptake due to endogenous (mammalian) TK. These two related measures are useful to evaluate the intensity of the images (e.g., high "sensitivity") and the ability to differentiate between HSV1-TK and endogenous-TK in the images (e.g., high "selectivity"). The "selectivity" measure is not interpreted as a relative sensitivity (i.e., a value of 1 indicating equal sensitivity) of the substrate to HSV1-TK vs. endogenous-TK. Neither of the measures represents a fraction of an ideal value (i.e., they do not have a maximum of one). They are intended for the direct comparison of substrates only.

A summary comparison of the "sensitivity" and "selectivity" is shown in Table 1. Note that the change in HSV1-TK expression was

TABLE 1

Figure 7B:
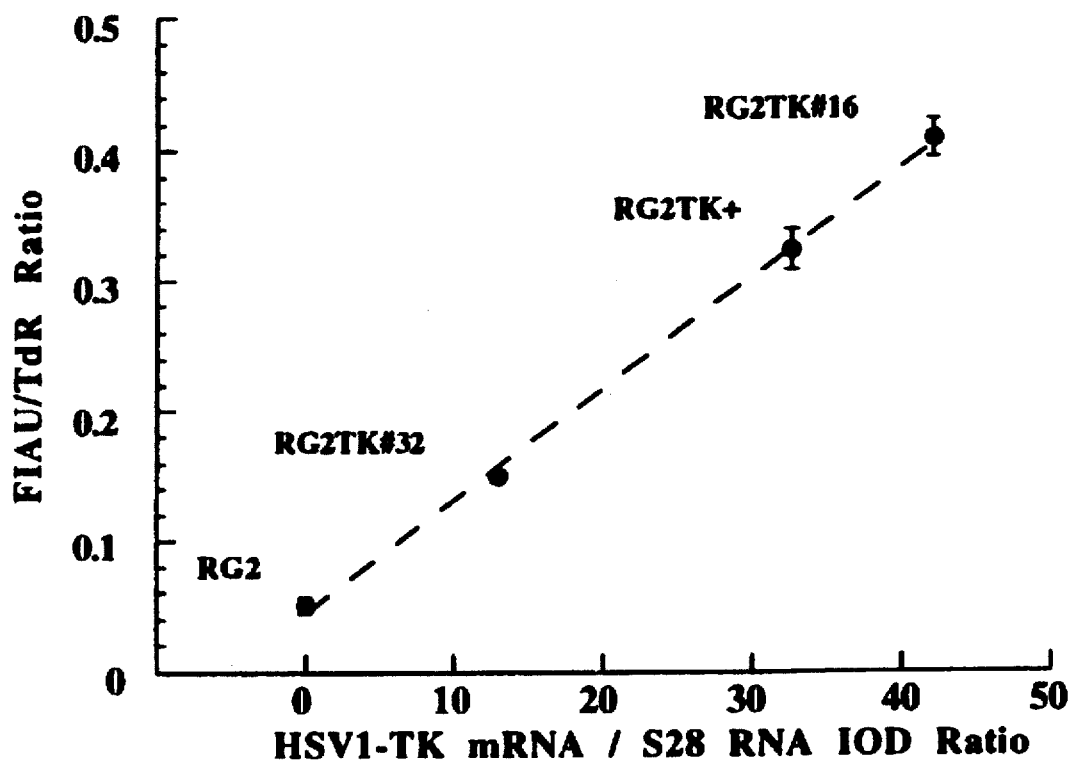

| | Data from FIG. 5 | | Data from FIG. 6A | | Data from FIG. 7B | |
|---|---|---|---|---|---|---|
| Substrate | Sensitivity* | Selectivity+ | Sensitivity* | Selectivity+ | Sensitivity* | Selectivity+ |
| FIAU | 0.0090 | 0.238 | 0.0105 | 0.179 | 0.0086 | 0.192 |
| Ganciclovir | 0.0004 | 0.143 | — | — | — | — |
| IUdR | 0.0029 | 0.006 | 0.0011 | 0.002 | — | — |

*Δ(substrate/TdR)/Δ(HSV1-TK mRNA/S28 RNA IOD)
+Sensitivity*/(substrate/TdR) for RG2 taken to be the difference in the HSV1-TK mRNA/S28 RNA IOD ratios. Therefore, the accumulation of ganciclovir™ by RG2TK+ cells was small compared to that of FIAU and IUdR and may not provide a sufficient signal for imaging and IUdR does not distinguish well between transduced RG2TK+ and non-transduced RG2 cells.

EXAMPLE 7

Animal preparation and tumor inoculation Two male Fisher 344 rats weighing 250±20 g were anesthetized with a gas mixture consisting of 2% Isoflurane, 70% nitrous oxide and 30% oxygen. A 2% lidocaine gel was applied to the ears and the head was fixed with a stereotaxic device. After midline scalp incision, a burr hole was made through the skull 1 mm posterior and 3 mm lateral to the bregma. The tumor cell suspensions were aspirated into a 50 μl gas tight Hamilton syringe (Ga. 25) and attached to a stereotaxic device. The syringe needle was then inserted 6 mm deep into the caudate nucleus and the cell suspension ($10^5$ cells in 10 μl) was slowly injected over 2 minutes. RG2TK+ cells were injected into the left hemisphere, and RG2 cells were injected into the right hemisphere. Bone wax was applied to cover the skull defect and the scalp was closed with 4.0 silk suture. Subcutaneous inoculations ($10^6$ cells in 50 μl) were also performed (RG2TK+ cells into the left flank and RG2 cells into the right flank). After the procedure, the animals were marked and placed in standard cages with water and Rodent LabChow #5001 (Purina Mills, Inc.) ad libitum. Comparison of different "marker substrates" for identifying HSV1-TK expression in animals After 10 days of tumor growth, both animals received i.v. injections of [$^{123}$I]-IUdR (400 uCi) and [$^{14}$C]-FIAU (10 uCi). Radioactivity was allowed to clear from the body over 24 hours to reduce tissue background activity, predominantly due to radiolabelled iodide, the major metabolite of [$^{123}$I]-IUdR. [Tjuvajev, J. G., Muraki, A., Ginos, J., Berk, J., Koutcher, J., Ballon, D., Beattie, B., Finn, R., and Blasberg, R., J. Nucl. Med., 34: 1152–62, 1993; Tjuvajev, J. G., Macapinlac, H. A., Daghighian, F., Scott, A. M., ginos, J. Z., Finn, R. D., Kothari, P., Desai, R., Zhang, Z., Beattie, B., Graham, M., Larson, S., and Blasberg, R. G., J. Nucl. Med., 35: 1407–17, 1994] The rats were killed at 24 hours under anesthesia; samples of tumor and adjacent tissue were disected and weighed, blood and plasma were obtained, and radioactivity was measured. Decay corrected $^{123}$I-radioactivity was assayed in a Packard AutoGamma 5550 Spectrometer; samples were stored in a refrigerator for 1 week to allow for $^{123}$I decay (>12 half lives) and $^{14}$C-radioactivity was measured in a Packard B1600 TriCarb beta spectrometer using external standard quench correction. Sample radioactivity was expressed as a percent of administered dose per gram of tissue or per unit volume of fluid.

Figure 8A:
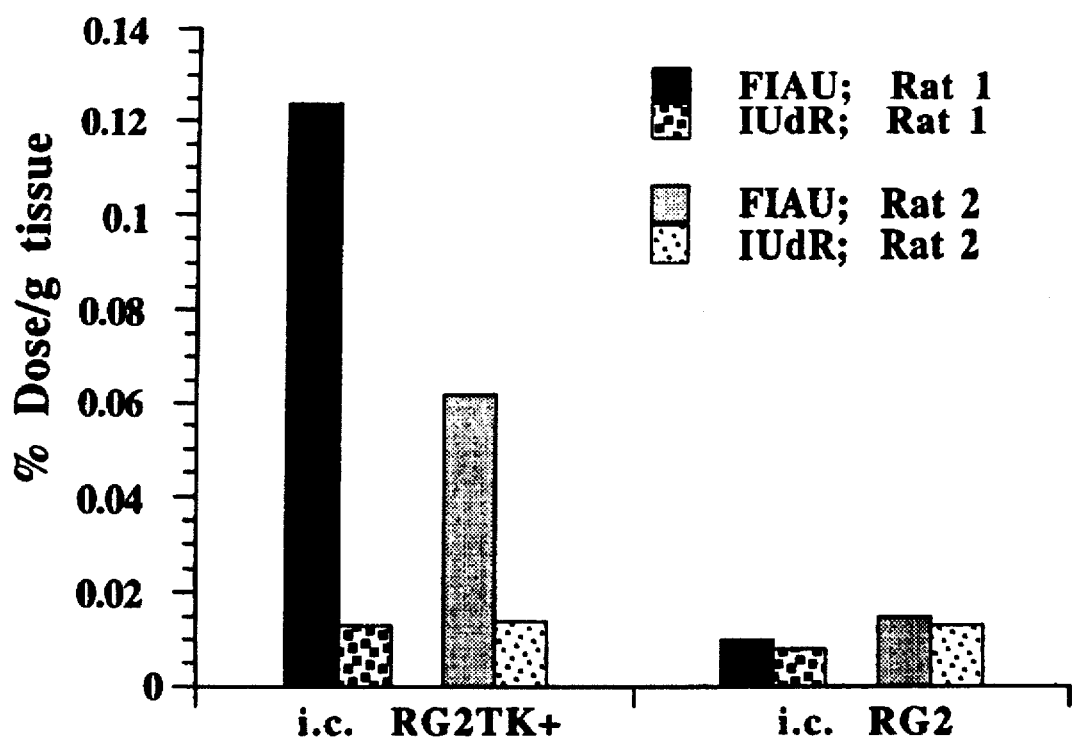
FIG. 8 shows the level of FIAU- and IUdR-derived radioactivity 24 h after administration in intracerebral and subcutaneous tumors. (A) intracerebral tumors. (B) subcutaneous tumors.
Figure 8B:
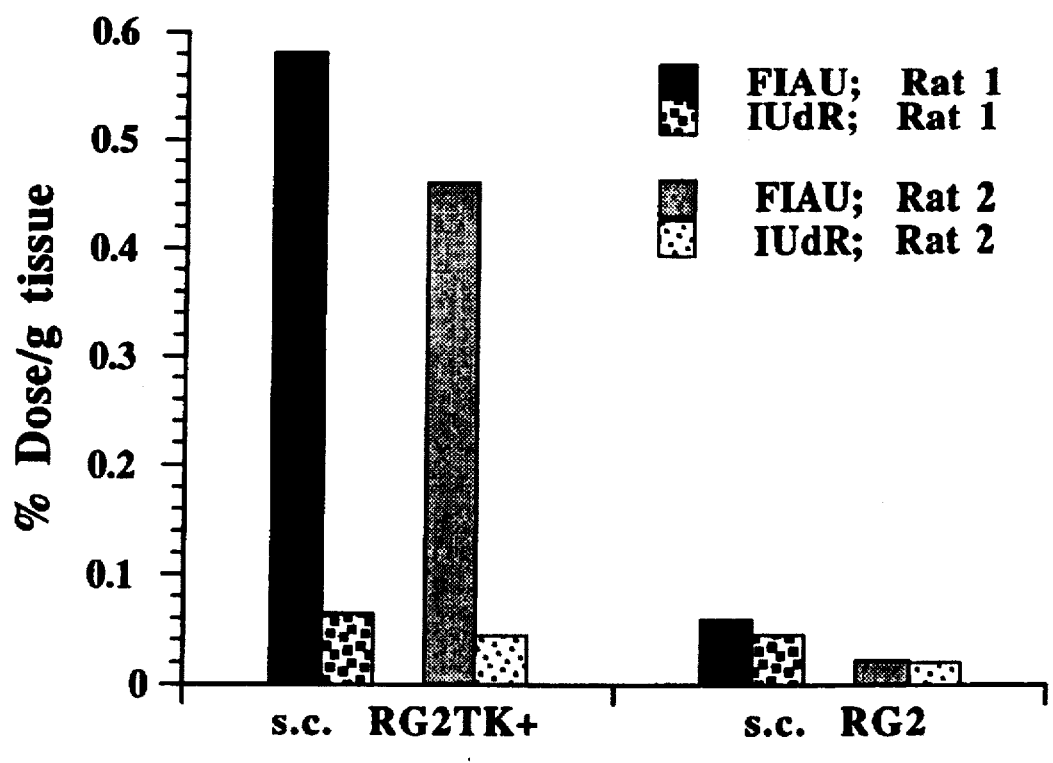
Figure 9A:
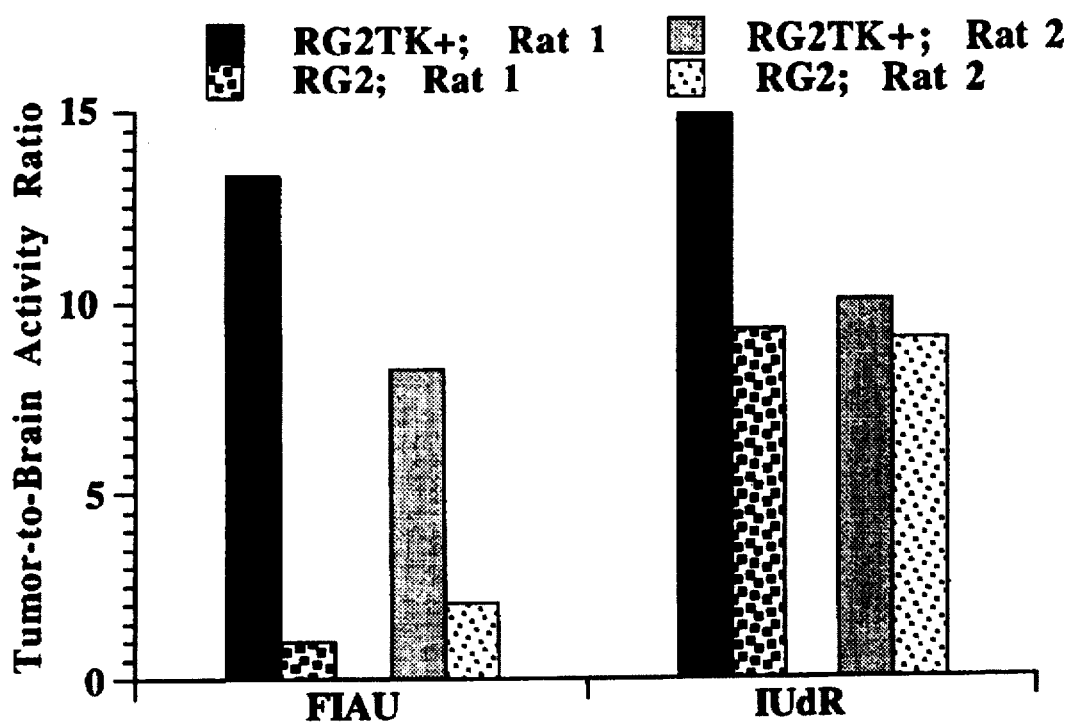
FIG. 9 shows a comparison of FIAU and IUdR-derived radioactivity in tumor cells transduced with a marker gene and non-transduced cells of adjacent tissue 24 h after administration. (A) intracerebral tumors. (B) subcutaneous tumors.
Figure 9B:
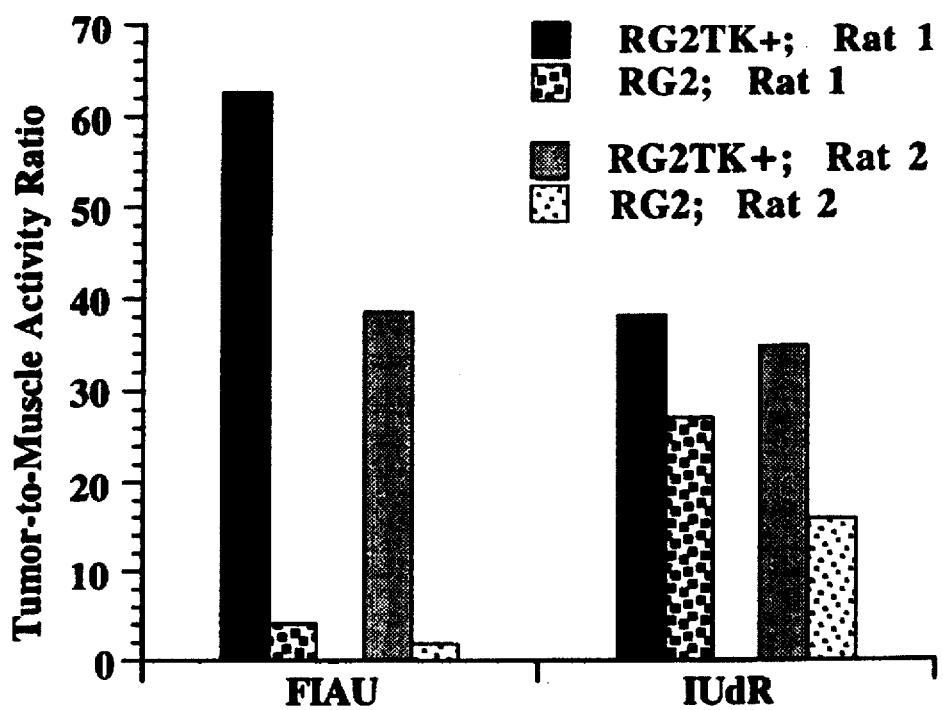

The level of FIAU- and IUdR-derived activity in the intracerebral (i.c.) and subcutaneous (s.c.) tumors is shown in FIG. 8. An important issue with respect to successful imaging of gene transfer is the comparison between radioactivity in tissue composed of cells that have been transduced with a "marker gene" and non-transduced cells of adjacent tissue. This comparison is illustrated in FIG. 9 for two potential "marker substrates" (FIAU and IUdR) of the HSV1-tk gene. The s.c. tumor-to-muscle ratios are shown in FIG. 9A, and the i.c. tumor-to-brain ratios are shown in FIG. 9B for transduced RG2TK+ and non-transduced RG2 tumors. For i.c. RG2TK+ tumors, the tumor-to-brain ratios of FIAU were 13.3 and 8.3, which was considerably higher than that for wild-type RG2 tumors 2.1 and 1.0 in these two animals (FIG. 9A). For s.c. RG2TK+ tumors, the tumor-to-muscle ratios of FIAU were very high 63 and 39, whereas the ratios for wild-type RG2 tumors were low 4.2 and 2.0 in these two animals.

Data analysis. Similar estimates of "sensitivity" and "selectivity" were obtained from animal data based on the accumulation of substrate in transduced and non-transduced tissue (percent dose per gram tissue, rather than on data normalized to TdR as was done in the tissue culture studies) and are shown in Table 2.

TABLE 2

| Substrate | RG2TK + /RG2 i.c. Tumors | | RG2TK + /RG2 s.c. Tumors | |
|---|---|---|---|---|
| | Sensitivity* | Selectivity+ | Sensitivity* | Selectivity+ |
| FIAU | 0.0025 | 0.201 | 0.0150 | 0.361 |
| IUdR | 0.0001 | 0.009 | 0.0007 | 0.020 |

*(uptake in RG2TK + tumor − uptake in RG2 tumor)/(HSV1-TK mRNA/S28 RNA IOD in RG2TK + cells)
+Sensitivity*/(uptake in RG2 tumor)

EXAMPLE 8

Selective imaging of HSV1-TK expression with FIAU in experimental animals. Two rats were prepared with i.c. RG2TK+ and RG2 tumors as described above. Sixteen days after RG2TK+ and RG2 cell innoculation, each animal was injected i.v. with 50 uCi of 2-[$^{14}$C]-FIAU and killed with euthanasia solution 24 hours later. The brain was rapidly extracted and frozen in preparation for cryosectioning and quantitative autoradiography (QAR). [Blasberg, Seminars in Neurology] The dried tissue sections were placed in an x-ray cassette along with 15 $^{14}$C-methyl methacrylate standards of known, previously calibrated radioactivity (4.4 to 2354 nCi/g tissue) and exposed to SB5 single coated X-ray film (Kodak) for 10 days. The resultant autoradiographic images reflect the spatial distribution of FIAU-derived $^{14}$C-radioactivity in the tissue sections. To convert the x-ray images to tissue radioactivity (nCi/g), the optical density of the standards was measured by computerized image analysis. A standard curve that relates mean optical density and tissue radioactivity was generated for each film. Knowing tissue radioactivity and the injected dose of 2-[$^{14}$C]-FIAU, the autoradiographic images are readily converted to parametric images of % dose/g tissue and gray-scale to a range of values.

Figure 10A:
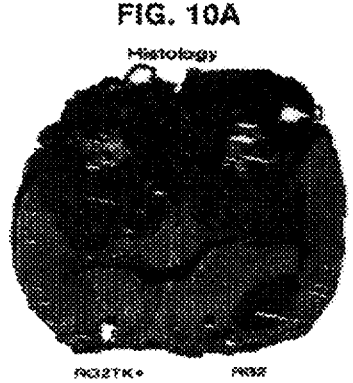
FIG. 10 shows imaging of HSV1-tk gene expression in vivo in RG2TK+ intracerebral tumors 24 h after administration. A) toluidine blue stained histological section; B) gray scaled quantitative autoradiographic images of 2-[$^{14}$C]-FIAU accumulation expressed as % administered dose per gram of tissue; C) gray scaled images of acid-rinsed adjacent section. The RG2TK+ tumor is located in the left hemisphere and non-transduced RG2 tumor is located in the right hemisphere.
Figure 10B:
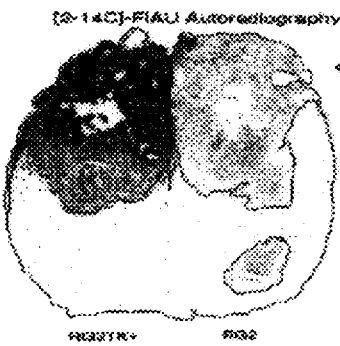

The ability to selectively image the expression of a "marker gene", HSV1-tk, in vivo is shown in FIG. 10. The histology and autoradiographic images were registered so that all regions of interest (ROIs) drawn would outline equivalent regions on the other images. The outline of the RG2TK+ and RG2 tumors in each hemisphere of the rat brain is clearly seen in the toluidine blue stained histological section (FIG. 10A). In the autoradiographic images (FIG. 10B), the RG2TK+ tumor is clearly visualized, whereas the RG2 tumor is barely detectable and the surrounding brain is at background levels. The punctuate heterogenous levels of FIAU activity observed in the RG2TK+ tumor (excluding the white areas representing tissue necrosis) are thought to reflect differences in HSV1-tk gene expression in the non-clonal, mixed population of transduced RG2TK+ cells growing intracerebrally. Quantitative analysis yielded mean activities of 0.180±0.140 and 0.22±0.024 % dose/g for the RG2TK+ and RG2 tumors, respectively. Peak activity in the RG2TK+ tumor was 0.43 % dose/g; adjacent brain activity was below the level of detection (<0.005% dose/g) on the autoradiograms.

Figure 10C:
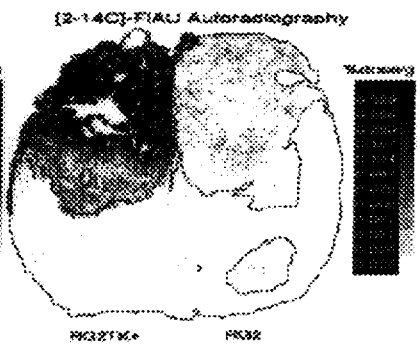

The tissue section used for autoradiography in FIG. 10C was adjacent to the one used in FIG. 10B; it was rinsed in acid solution (10% TCA) for 4 hours to remove nonincorporated FIAU and radiolabelled metabolites prior to autoradiographic exposure. Rinsing tissue sections had little effect on the distribution and amount of radioactivity measured in the autoradiogram (compare FIGS. 10B and 10C). This indicates a very low background activity due to soluble radiolabelled metabolites and demonstrates the value of using an "in vivo washout" strategy (imaging 24 hours after FIAU administration) to reduce background radioactivity.

EXAMPLE 9

Imaging in vivo transfection of RG2 tumors by the STK retrovirus in experimental animals. To assess whether FIAU imaging was sufficiently sensitive to monitor in vivo transfection of RG2 cells with the STK retrovirus, wild-type RG2 cells and gp-STK-A2 vector-producer cells (1:1 ratio) were co-implanted into the right hemisphere. The left hemisphere was inoculated with gp-STK-A2 vector-producer cells only. Ten days after inoculation, animals were injected i.v. with 50 uCi of 2-[$^{14}$C]-FIAU, killed 24 hours later and the brain was processed for QAR and histology. The HSV1-tk transfected tumor was well visualized on the autoradiographic image (FIG. 11B). In this case, the pattern of FIAU activity reflects spatial heterogeneity in the efficiency of retroviral transfection as well as differences in HSV1-tk gene expression. Surrounding normal brain and the area inoculated only with gp-STK-A2 vector-producer cells are poorly or not at all visualized. Histologic analysis of this area (FIG. 11A) showed an inflamatory reaction with perivascular infiltrates; the outlined area was heavily infiltrated and almost all vector-producer cells were rejected. Rinsing tissue sections in acid solution for 4 hours prior to X-ray film exposure had little effect on the distribution and amount of radioactivity measured in the transduced tumor, but eliminated the low level of radioactivity localized to the area of the left hemisphere that was inoculated with gp-STK-A2 vector-producer cells (FIG. 11C) indicating that the low level activity in this region of the left hemisphere was not incorporated into macromolecules. Quantitative analysis yielded mean activities of 0.34±0.24% dose/g for the in vivo transduced RG2 (TK+) and 0.028±0.023% dose/g for the gp-STK-A2 vector-producer cell inoculated area prior to rinsing. Peak activity in the in vivo transduced RG2(TK+) tumor was 0.96% dose/g; adjacent brain activity was below the level of detection on the autoradiograms.

EXAMPLE 10

Effect of timing on selective imaging of HSV1-TK expression with FIAU. To assess the appropriate timing for HSV-TK "marker gene" imaging with FIAU, rats were also killed 4 hours after tracer injection. The animal shown in FIG. 12 received i.c. innoculations of wild-type RG2 and clone #16 (RG2TK#16) in opposite hemispheres and was studied 14 days later. The autoradiographic images were obtained 4 hours after tracer administration. There is only a small difference in amount of FIAU radio-activity localized to the transduced compared to the non-transduced tumor in the "non-rinsed" autoradiogram (FIG. 12B). This animal was quite ill, and the high levels of plasma radioactivity and breakdown of the BBB largely accounted for this pattern of radioactivity. This becomes evident when comparing the "non-rinsed" and "rinsed" images (FIGS. 12B and 12C, respectively). Comparing the 4 and 24 hour "non-rinsed" images (FIG. 12B to FIGS. 10B and 11B) demonstrates the value of using a "washout" imaging strategy (imaging 24 hours after FIAU administration) to reduce background radioactivity.

The "sensitivity" and "selectivity" measures for the autoradiographic data are shown in Table 3. These values are in the same units as the tissue sampling results in Table 2. They are based on measurements of % dose/g in three animals (2 RG2TK+ and 1 RG2TK#16), rather than on data normalized to TdR as was done in the tissue culture studies (Table 1).

TABLE 3

| Substrate | RG2TK + /RG2 i.c. Tumors[+] FIG. 9 | | RG2TK#16/RG2 i.c. Tumors[+] Figure not shown | |
|---|---|---|---|---|
|  | Sensitivity[*] | Selectivity[+] | Sensitivity[*] | Selectivity[+] |
| FIAU | 0.0039 | 0.165 | 0.0058 | 0.222 |

[*]Δ(substrate % dose/g)/Δ(HSV1-TK mRNA/S28 RNA IOD)
[+]Sensitivity[*]/(uptake in RG2 tumor)

EXAMPLE 11

Selection of 2'-fluoro-1-β-D-ribofuranosyl analogues of uracil. The 2'-fluoro-arabinofuranosyl nucleoside analogues were originally synthesized [Watanabe, K., Reichman, U., Hirota, K., Lopez, C., and Fox, J., J. Med. Chem., 22: 21–24, 1979], developed as potential antiviral and/or antineoplastic agents [Fox, J. J., Lopez, C., and Watanabe, K. A. In: Medicinal Chemistry Advances, edited by De Las Heras, F. G., ana Vega, S., Pergamon, Oxford, pp. 27–40, 1981], and later radiolabelled. Several 2'-fluoro-ribofuranosyl nucleoside analogues were subsequently synthesized and radiolabelled [Iwashina, T., Tovell, D. R., Xu, L., Tyrrell, D. L., Knaus, E. E., and Wiebe, L. I., Drug Design and Delivery, 3: 309–21, 1988; Morin, K. W., Wiebe, L. I., and Knaus, E. E., Carbohydrate Res., 249: 109–16, 1993; Mercer, J. K., Xu, L. H., Knaus, E. E., and Wiebe, L. I., J. Med. Chem., 32: 1289–94; Mercer, J. R., Knaus, E. E., and Wiebe, L. I. J. Med. Chem., 30: 670–5, 1987] Synthesis of the 2'-fluoro-ribofuranosyl nucleosides is considerably easier than that of the 2'-fluoro-arabinofuranosyl compounds, although more data has been published with the 2'-fluoro-arabino than the 2'-fluoro-ribo nucleoside analogues.

Passage of the nucleosides across the blood brain barrier (BBB) is an important factor to consider in the design of radiolabelled 2'-fluoro-nucleoside analogues for imaging HSV1-TK expression in the brain. A specific nucleoside (thymidine) transporter is absent from normal brain capillaries. This suggests that the 2-fluoro-nucleoside analogues are not actively transported across the normal BBB. It is known that brain capillary permeability for many compounds is related to their octanol/water partition coefficient (P) and molecular weight. [Levin, V. N. J. Med. Chem., 23: 682–4, 1980] Several authors have described a relationship between the brain capillary permeability and log P or log P·$D_m$, where $D_m$ is a measure of diffusibility. The optimal range of log P values for compounds to cross the BBB by virtue of their lipid solubility is between 0.9 to 2.6. [Dischino, D. D., Welch, M. J., Kilbourn, M. N., and Raichle, M. E., J. Nucl. Med., 24: 1030–8, 1983] The permeability-surface area product (PS) of normal brain capillaries was estimated from the measured octanol-water partition coefficients and the molecular weights using the relationship: log(PS)=5.2+log(P·$D_m$), where $D_m \approx 10^{-4}$·MW$^-$ ½. Fenstermacher, J. D. Drug transfer across the blood brain barrier. In: Topics in Pharmaceutical Sciences. Ed.: Breimer, D. D., and Speiser, P. Amsterdam: Elsevier, pp. 143–54, 1983; Fenstermacher, J. D., and Rapoport, S. I. In: Handbook of Physiology. The Cardiovascular System. Microcirculation. Bethesda, Md.: Am. Physiol. Soc., sect. 2, Vol. IV, pt. 2, chapt. 21, p. 969–1000, 1984; Fenstermacher, J. D. In: Implications of Blood-Brain Barrier and Its Manipulation. Basic Science Aspects. Ed. by Neuwelt, E., New York: Plenum, Vol. 1, Chapt. 6, pp. 132–55, 1988]

The lipophilicity data for several 2'-fluoro-nucleoside analogues is shown in Table 4. The log P values for 5-halo-2'-fluoro-arabino-2'-deoxyuracils (ranging from −0.26 to −1.09) are slightly lower than those for corresponding 5-halo-2'-fluoro-ribo-2'-deoxyuracil analogues (ranging from −0.14 to −1.09. [Xu, L., Gati, W. P., Knaus, E. E., and Wiebe, L. I. In: Advances in Radiopharmacology. Eds: Maddalena, D. J., Snowdon, G. M., Boniface, G. R., Univ. of Wollongong Printing Service, Wollongong, Australia, pp. 283–298, 1990] Lipophilicity also increases with the increase in size of substituting groups in the 5-position of the pyrimidine ring. Based on the data in Table 3, the PS product of brain capillaries for 2'-fluoro-nucleoside analogues increases in the following order: FFAU<FMAU23 FEAU≦FIRU≦FIAU<<FIVRU≦(FIVAU).

250×4.6 mm reverse phase 10 micron $^{18}$C column (Phenomenex), the isocratic mobile phase of 15% methanol in 0.05M potassium phosphate buffer (pH 5) and at a flow rate of 2 ml/min. The no carrier-added [$^{131}$I]-FIAU synthesis yielded a 93% pure, pyrogen-free compound with high a specific activity approaching no carrier added concentration that is suitable for diagnostic procedures in humans. Three radioactive peaks were detected: 1) [$^{131}$I]-iodine (2.7 min) 2%; 2), 5-[$^{131}$I]-iodouracil (6 min) 5%; and 3) 5-[$^{131}$I]-2'-F-β-D-arabino-furanosyl-uracil (8.7 min) 93% of total radioactivity of the injected sample. The elution times of these three [$^{131}$I]-compounds were identical to those obtained with corresponding standards: [$^{131}$I]-iodide,

TABLE 4

Lipophilicity (log P) of different for 2'-fluoro-nucleoside analogues and calculated permeability surface area product (PS) of the cerebral capillaries.

| | Log P⁺ | Log P* | MW | D m | PS⁺ | PS* | | Log P⁺ | Log P* | MW | D m | PS⁺ | PS* |
|---|---|---|---|---|---|---|---|---|---|---|---|---|---|
| Nucleosides | | | | | | | 5-halo-2'-deoxyuridines | | | | | | |
| UdR | −1.48 | −.131 | 228 | 6.62 | 0.03 | 0.05 | 5-FUdR | −1.51 | −1.52 | 246 | 6.37 | 0.03 | 0.03 |
| TdR | −1.12 | −0.80 | 242 | 6.43 | 0.08 | 0.16 | 5-IUdR | −0.76 | −.089 | 354 | 5.31 | 0.14 | 0.11 |
| | | | | | | | 5-IVdU | — | 1.10 | 380 | 5.13 | — | 10.29 |
| 5-(halo/other)-2'-fluoro-ARABINO-2'-deoxyuracils | | | | | | | 5-(halo/other)-2'-fluoro-RIBO-2'-deoxyuracils | | | | | | |
| FFAU | — | −1.09 | 264 | 6.15 | | 0.08 | FFRU | — | −1/68 | 264 | 6.15 | — | 0.02 |
| FIAU | −0.14 | −0.14 | 373 | 5.18 | 0.59 | 0.59 | FIRU | — | −0.26 | 373 | 5.18 | — | 0.45 |
| FMAU | — | — | 398 | 5.01 | — | — | FIVRU | — | 1.21 | 398 | 5.01 | — | 13.03 |
| FEAU | −0.62 | — | 261 | 6.19 | 0.23 | — | | | | | | | |
| | −0.49 | — | 275 | 6.03 | 0.31 | — | | | | | | | |
| Reference BBB Markers | | | | | | | | | | | | | |
| AIB | — | −2.48 | 103 | 9.85 | 0.00052 | — | | | | | | | |
| DTPA | — | −3.89 | 550 | 4.26 | 0.00009 | — | | | | | | | |

*log P values were measured; PS values were calculated.
⁺log P values published by Xu, et al. (1994) [Xu, L., Gati, W. P., Knaus, E. E., and Wiebe, L. I. In: Advances in Radiopharmacology. Eds: Maddalena, D. J., Snowdon, G. M., Boniface, G. R., Univ. of Wollongong Printing Service, Wollongong, Australia, pp. 283–298, 1990]*; PS values were calculated.

The radiolabelled 2'-fluoro-nucleoside analogues are prepared by the following procedures:

5-[$^{131}$I]-FIAU synthesis. The synthesis of a key intermediate, (i) 3-O-acetyl-5-benzoyl-2'-deoxy-2'-fluoro-D-arabino-furanosyl bromide, was previously developed. [Reichman, U., Watanabe, K. A., and Fox, J. J., Carbohydr. Res., 42: 233–40, 1975] Condensation of the halogenose intermediate (i) with trimethlsilylated uracil and subsequent removal of the blocking groups by saponification results in another intermediate (ii). Removal of the acyl-protecting groups on (ii) during iodination [Watanabe, K., Reichman, U., Hirota, K., Lopez, C., and Fox, J., J. Med. Chem., 22: 21–24, 1979] produces the 5-iodo radiolabelled nucleoside. No carrier-added $^{131}$I-labelled [$^{131}$I]-FIAU was prepared by reacting FAU with carrier-free $^{131}$I-labelled sodium iodide using iodogen followed by isolation of the product by column chromatography. The radiochemical yield of $^{131}$I-FIAU is approximately 80%, similar to that of $^{131}$I-IUdR. The $^{131}$I-FIAU injection solution was prepared by evaporation of the methanol-eluted fraction from the C$_{18}$ cartridge and dissolving the residue in a sterile pyrogen-free physiological saline solution and passage through a sterile non-pyrogenic 0.22 μm Millipore™ filter.

Radiochemical purity of 5-[$^{131}$I]-FIAU. HPLC procedures were performed on a system consisting of a HPXL Pump (Rainin Instrument Co., Inc.), Flo-One Beta detector Series 100 (Radiomatic), ultraviolet detector Spectroflow 757 (Kratos, Inc.). Data was collected and analyzed using online Dynamax™ software (Rainin). HPLC conditions:

2-[$^{14}$C]-5-iodo-uracil, and 2-[$^{14}$C]-2'-fluoro-5-iodo-1-β-D-arabinofuranosyl-uracil (2-[$^{14}$C]-FIAU).

5-[$^{18}$F]-FFAU synthesis. Initial steps of synthesis of 5-[$^{18}$F]-FFAU are similar to those of $^{131}$I-FIAU, and are also achieved by condensation of the halogenose intermediate (i) with trimethlsilylated uracil. Subsequent removal of the blocking groups by saponification to an intermediate product and yields FAU. Radiolabelling of the FAU with [$^{18}$F]to obtain 5-[$^{18}$F]-FFAU was accomplished using actyl hypofluorite-[$^{18}$F] in glacial acetic acid solvent. The preparation, formulation and clinical application of the radiopharmaceutical 5-[$^{18}$F]-FUdR, without 2'-F "up" protective group in the sugar moiety, from 3,5-di-O-acetyl-2'-deoxy-uridine and [$^{18}$F]-radiolabelled acetyl hypofluorite has been performed previously to study the intrahepatic and systemic infusion of 5-[$^{18}$F]-FUdR in patients with liver methastases of colorectal carcinoma. [Bading, J., Sigurdson, E., Finn, R., Yeh, S., Ginos, J., Kemeny, N., and Larson, S., Drug Metab. Disp., 22: 643–650, 1994] Using this electrophilic approach to radiolabelling, a nominal 45-minute irradiation with a beam current of 15–25 μA, 10–20 mCi of 5-[$^{18}$F]-FFAU was obtained as a neutral, isotonic, sterile and pyrogen-free radiopharmaceutical within 45–60 minutes. Although the yield and specific activity are dependent on the carrier elemental fluorine concentration and the target recovery of [$^{18}$F]-F$_2$, typical radiochemical yields with 5-[$^{18}$F]-FUdR approached 30% with radiochemical purity in excess of 97%, and specific activity at the end of synthesis.

The presence of hydroxyl groups does not necessarily affect the fluorination using acetyl hypofluorite. [Visser, G.

W. M., Noorhuos, O., Zwaagstra, O., Herscheid, J. D. M., and Hoekstra, A. Int. J. Radiat. Isot., 37: 1074–76, 1986; Ehrenkaufer, R. E., Potocki, J. F., and Jewitt, D. M., J. Nucl. Med., 25: 33, 1984; Van Rijn, D. J. S., Herscheid, J. D. M., Visser, G. W. M., and Hoekstra, A. J Appl. Radiat. Isot. 36: 111, 1985] The presence of a fluorine atom in 2'-up position did not significantly compromise the successful synthesis of 5-[$^{18}$F]-FFAU using the electrophilic approach.

2-[$^{11}$C]-FMAU Synthesis. 2'-Fluoro-5-[$^{11}$C]-methyl-1-β-D-arabinosuranosyl-uracil ([$^{11}$C]-FMAU) is made in good yield using selective alkylation of pyrimidyl dianion and [$^{11}$C]-methyl-iodide. [Conti, P. S., Alauddin, M. M., Fissekis, J. R., Schmall, B., and Watanabe, K. A. Synthesis of 2'-fluoro-5-[$^{11}$C]-methyl-1-β-D-arabinosuranosyl-uracil ([$^{11}$C]-FMAU): a potential nucleoside analog for in vivo study of cellular proliferation with PET. Briefly, 3',5'-o-Bis-

TABLE 5

| Abbr. | Chemical Name | Label | Rationale |
|---|---|---|---|
| FIAU | 2'-fluoro-5-iodo-1-β-D-arabinofuranosyl-uracil | 2-[$^{14}$C]* 5-[$^{131}$I]* | developed as an antiviral agent, high uptake in HSV infected cells |
| FFAU | 2'-fluoro-5-fluoro-1-β-D-arabinofuranosyl-uracil | 5-[$^{18}$F]* | developed as an antiviral agent, high uptake in HSV infected cells |
| FMAU | 2'-fluoro-5-methyl-1-β-D-arabinofuranosyl-uracil | 2-[$^{14}$C]* 5-[$^{11}$C]-methyl | developed as an antiviral agent, high uptake in HSV infected cells |
| FEAU | 2'-fluoro-5-ethyl-1-β-D-arabinofuranosyl-uracil | 2-[$^{14}$C]* 5-[$^{11}$C]-ethyl** | developed as an antiviral agent, high uptake in HSV infected cells |
| FEFAU | 2'-fluoro-5-(2-fluoro-ethyl)-1-β-D-arabinofuranosyl-uracil | 5-(2-[$^{18}$F]-ethyl) | developed as an antiviral agent, comparable to acyclovir activity, low toxicity in vitro |
| FIVAU | 2'-fluoro-5-iodovinyl-1-β-D-arabinofuranosyl-uracil | 5-[$^{131}$I]-iodovinyl | developed as an antiviral agent, high octanol-water partition coefficient, high uptake in HSV infected cells |
| FIRU | 2'-fluoro-5-iodo-1-β-D-ribofuranosyl-uracil | 5-[$^{131}$I] | developed for viral imaging, high uptake in HSV infected cells, ideal for 24 hr "washout" imaging |
| FIVRU | 2'-fluoro-5-iodovinyl-1-β-D-ribofuranosyl-uracil | 5-[$^{131}$I]-iodovinyl | developed for viral imaging, high octanol-water partition coefficient, high uptake in HSV infected cells, ideal for 24 hr "washout" imaging |

*Available Moravek.

Synthesis of Nucleosides of ω-Fluoroalkyluracil Nucleosides (Starting Materials). The prerequisite 2-fluoro-β-D-arabinofuranose was originally synthesized from diacetone-D-glucose. [Reichman, U., Watanabe, K. A., and Fox, J. J., Carbohydr. Res., 42: 233–40, 1975] Tann, et al. reported a shorter synthesis of the fluoro-sugar. [Tann, C. H., Brodfuehrer, P. R., Brundidge, S. P., Sapino, C., and Howell, H. G. J. Org. Chem., 50: 3644–3648, 1985] However, the newer procedure requires high pressure HF in a sealed vessel, and removal of small amounts of impurity [2-O-(3-hydroxybutyl 1-2-hydrosyethyl)-1,3,5-tri-O-benzoyl-D-arabinose] by chromatography was difficult. The method was developed based on the fact that introduction of a substituent on the C2 position of the sugar by nucleophilic reaction is difficult, especially when the nucleophile is weak (such as fluoride). However, nucleophilic substitution at the C3 position of carbohydrate is much easier. Thus, synthetic 3-fluoro-hexose (glucose) was converted into 2-fluoro-arabinose (pentose) by removal of the anomeric carbon. The original procedure is modified to prepare the desired sugar in a much simpler and more economic manner. Originally, diacetone-D-glucose was converted into diacetone-D-allose by ruthenium catalyzed oxidation followed by reduction. Swern oxidation is used instead of the ruthenium catalyst. Diacetone-D-allose is then tosylated and then subjected to fluorination. Purification of the product 3-fluoro-diacetone-D-glucose is difficult due to the presence of unreacted 3-O-tosyl intermediate. Therefore, mesyl is used instead of the tosyl intermediate since after fluorination the fluorinated product can be extracted with petroleum ether from a water-diluted reaction mixture, while the unreacted mesyl derivative stays in aqueous solution. This new procedure does not require any chromatographic separation of intermediates throughout the synthesis.

5-[$^{131}$I]-FIRU synthesis. Radiolabeling procedures described for 5-[$^{131}$I]-FIAU are carried out except utilizing 2'-fluoro-ribo-derivative as starting material.

(tetrahydropropyranyl)-2'fluoro-1-β-D-arabino-furanosyl-uracil in dry THF was allowed to react with a trace of n-butyllithium at –78° C. Carbon-11-labelled methyl iodide prepared according to Langstrom, B., and Lundquist, H., Int. J. Appl. Radiat. Isotopes, 27: 357, 1975, is introduced into the cooled reaction solution. The mixture is warmed to room temperature at which time 2N HCL in methanol is introduced. Hydrolysis is achieved by reflux caused by heating the vessel to 110° C. for 3 minutes. Following removal of the solvent by evaporation and neutralization of the residue, the crude product is dissolved in 10% acetonitrile in water and injected onto a C-18 reverse phase semi-preparative column. Elution of the product is achieved using the 10% acetonitrile/water solvent and a flow rate of 4 ml/min. The product is reported to elute with a retention time of 9.7 minutes.

[$^{11}$C]-FEAU Synthesis. 5-([$^{11}$C]-Ethyl)-2'fluoro-1-β-D-arabinosuranosyl-uracil ([$^{11}$C]-FEAU) is carried out using similar reaction conditions as for [$^{11}$C]-FMAU, but substituting carbon-11-labelled ethyl iodide for methyl iodide. Carbon-11-labelled ethyl iodide is prepared from the Grignard reaction of methylmagnesium bromide with [$^{11}$C]-CO$_2$ followed by addition and reflux with hydroiodic acid.

[$^{18}$F]-FEFAU Synthesis. 5-(2-[$^{18}$F]-fluoro-ethyl)-2'-fluoro-1-β-D-arabinofuranosyl-uracil ([$^{18}$F]-FEFAU) synthesis is effected using either of the following methods:

Method A: 1-(2'-Fluoro-3-O-acetyl-5-O-benzoyl-β-D-arabinofuranosyl)-5-(2-hydroxyethyl)-uracil is prepared by condensation of 5-(2-hydroxyethyl)-uracil with the bromo-sugar by the silyl procedure. The product is benzoated at N3 and then treated with DAST. After mild saponification of acyl protecting groups, FEFAU is obtained. The N3 benzoyl protection is necessary. 5-(2-Hydroxyethyl)-uracil nucleoside is treated with DAST, giving the cyclized fluoropyrimidine nucleoside. N3 protection reduces nucleophilicity of the carbonyl group of the uracil ring. [Matsuda, A., Yasuoka, J., and Ueda, T., Chem. Pharm. Bull., 37: 1659–61, 1989]

Method B: 1-(2'-Fluoro-3-O-acetyl-5-O-benzoyl-β-D-arabinofuranosyl)-5-(2-hydroxyethyl)-uracil is converted into the 5-(2-bromo-ethyl)-derivative. Conversion of the latter into the N2,O3,O5'-tribenzoyl derivative followed by treatment with $^{18}F^-$ gives the tribenzoyl derivative of $[^{18}F]$-FEFAU. Saponification of the benzoyl groups completes the synthesis of $[^{18}F]$-FEFAU.

[*I]-FIVAU and [*I]-FIVRU Synthesis. Radiolabelled [*I]-FIVAU and [*I]-FIVRU are labelled with $[^{131}I]$, $[^{124}I]$ or $[^{123}I]$. [Iwashina, T., Toyell, D. R., Xu, L., Tyrrell, D. L., Knaus, E. E., and Wiebe, L. I., Drug Design and Delivery, 3: 309–21, 1988] [*I]-FIVAU and [*I]-FIVRU synthesis is as follows:

Reaction of 1-(2-deoxy-2-fluoro-β-D-ribofuranosyl)-5-iodouracil (1b), prepared by reaction of 1a [Morin, K. W., Wiebe, L. I., and Knaus, E. E., Carbohydrate Res., 249: 109–16, 1993; Codington, J. F., Doerr, I. L. and Fox, J. J., J. Org. Chem., 29: 558–564, 1964] with sodium iodide in the presence of nitric acid [Mercer, J. R., Ph.D. Thesis, University of Alberta, Edmonton, Alberta, Canada, Apr. 6, 1985] with ethyl acrylate, bis(triphenylphosphine)palladium(II) chloride and triethylamine, using a modified procedure reported by Jones, A. S., Verhelst, G. and Walker, R. T., Tetrahedron Lett., 45: 4415–4418, 1979, yielded the (E)-5-(2-ethoxycarbonyl-vinyl) analogue (2) in 55% chemical yield. Alkaline hydrolysis of 2 afforded the (E)-5-(2-carboxyvinyl) derivative (3) (52% yield), which, after reaction with molecular iodine generated in situ, yielded (E)-5-(2-iodovinyl)-1-(2-deoxy-2-fluoro-β-D-furanosyl)-uracil (4a) in 28% yield (see Scheme 1). Similar reaction of 3 with 'carrier-added' $[^{125}I]$-NaI gave $[^{125}I]$-4b in, 67.8% radiochemical yield; its specific activity was 823 MBI/μmol. Similar reaction of 3 with 'carrier-added' $[^{131}I]$-NaI gave $[^{131}I]$-4e in 47.3% radiochemical yield; its specific activity was 10.4.3 MBI/μmol. The arabino- derivative related to 4b, i.e., $[^{125}I]$-IVFAU (1b), was synthesized similarly by reaction of 5 (X-COOH) with 'carrier-added' $[^{125}I]$-NaI in 61.6% radiochemical yield; its specific activity was 138.5 MBI/μmol$^{-1}$. The radioiodination reaction described is also suitable for incorporation of the short-lived isotope $^{123}I$ ($t_{1/2}$, 13.26 hr), and is applicable to 'no carrier-added' synthesis.

(E)-5-(2-Ethoxycarbonylvinyl)-1-(2'-deoxy-2'-fluoro-1-β-D-ribofuranosyl)-uracil (2).

Dry triethylamine (0.23 mi), ethyl acrylate (0.23 ml, 2.12 mmol), and bis(triphenyl-phosphine)palladium(II) chloride (3.8 mg) were added consecutively to a solution of 1b (0.237 g, 0.637 mmol) in dry acetonitrile (8 ml), and the reaction was allowed to proceed at 77° C. with stirring for 24 hr. The reaction mixture was allowed to cool to 25° C., filtered, and the filtrate was evaporated in vacuo. The residue was purified by silica gel flash column chromatography using methanol:chloroform (1:9 v/v) as eluant. After removal of the solvent in vacuo from the fractions containing 2, the product was recrystallized from chloroform:methanol to give 2 as white needles (0.12 g, 54.8%).

(E)-5-(2-Carboxyvinyl)-1-(2'-deoxy-2'-fluoro-β-D-ribofuranosyl)-uracil (3).

A solution of 2 (0.126 g, 0.399 mmol) in 0.5N KOH (4 ml) was allowed to stir at 25° C. for 2 hr prior to neutralization with Dowex 50× 8–200 ion-exchange resin (H+). The mixture was filtered, the solvent was removed in vacuo, and the residue was recrystallized from acetonitrile: methanol to yield 3 as white crystals (60 mg, 52%).

(E)-5-(2-Iodovinyl)-1-(2'-deoxy-2'-fluoro-β-D-ribofuranosyl)-uracil (4a).

Sodium iodide (18 mg, 0.12 mmol), potassium acetate (18 mg) and 98% ethyl alcohol (0.35 ml) were added consecutively to a solution of 3 (35 mg, 0.111 mmol) in dry dimethylformamide (4 ml). The mixture was allowed to stir for 10 min, chloramine-T (35 mg, 0.154 mmol) was then added, and the reaction was allowed to proceed for 90 min at 25° C. with stirring. Removal of the solvent in vacuo gave a residue which was purified by elution from a silica gel flash column using methanol:chloroform (1:9 v/v) as eluant. The fraction containing 4a was purified by preparative TLC using methanol:chloroform (1:9 v/v) as development solvent. Extraction of the ultraviolet-active spot with methanol:chloroform (1:4 v/v), followed by removal of the solvent in vacuo, and trituration of the residue with chloroform, yielded 4a as a white solid mass (12.5 mg, 28%).

(E)-5-(2-$[^{125}I]$-Iodovinyl)-1-(2'-deoxy-2'-fluoro-β-D-ribofuranosyl)-uracil (4b).

Solutions of the sodium iodide (50 μg, 0.33 μmol) in ethanol (100 μl), and of potassium acetate (500 μg) in ethanol (50 μl), and 3 (0.5 mg, 1.45 μmol) were added to a 1 ml reaction vial. The solvent volume was reduced to approximately 20 μl under nitrogen, and $[^{125}I]$-NaI (27.84 MBq) in ethanol (10 μl) and dry dimethylformamide (100 μl) were added. The resulting mixture was stirred for 10 min, and then a solution of chloramine-T (200 μg) in dry dimethylformamide (20 μl) was added. The reaction was allowed to proceed for 90 min at 25° C. with stirring. The solvent was then removed under a stream of nitrogen, and the residue was purified by preparative HPLC using methanol:water (1:1 v/v) as eluant with a flow rate of 1.4 ml/min. The radioactive fraction corresponding to that of authentic material of retention time 21 min, was 4b in 67.78% radiochemical yield (18.8 MBq) with a specific activity of 82.3 MBI/μmol.

(E)-5-(2-$[^{131}I]$-Iodovinyl-1-(2'-deoxy-2'-fluoro-β-D-ribofuranosyl)-uracil (4c).

4c was prepared by the procedure described above for 4b but using $[^{131}I]$-NaI. The radiochemical yield was 47.3%, and the specific activity was 104.3 MBq/μmol.

(E)-5-(2-$^{131}I$]-Iodovinyl)-1-(2'-deoxy-2'-fluoro-β-D-arabinofuranosyl)-uracil (5b).

5b was synthesized by reaction of 5 (X-COOH) with 'carrier-added' $[^{125}I]$-NaI, using the procedure described for the synthesis of 4b. The radiochemical yield was 61.6% and the specific activity was 138.5 MBq/μmol.

DISCUSSION

Gene therapy for the treatment of human diseases is currently being explored, and several approaches are being tested in patients [Culver, K. W., and Blaese, R. M., Trends in Genetics, 10: 174–178 (1994)]. A non-invasive, clinically applicable method for imaging successful in vivo gene transfer and expression in target tissue or specific organs of the body would be useful; it would facilitate the monitoring and evaluation of gene therapy in human subjects by defining the location, magnitude and persistence of gene expression over time.

Clinical monitoring of gene targeting, transfer and expression requires the appropriate combination of "marker gene" and "marker substrate" characteristics. The following characteristics are ideal if not essential: (1) A "marker gene" is chosen that is not present (or not normally expressed) in host tissue and the gene product is an enzyme that can be expressed in host cells. This enzyme must be non-toxic to host cells and catalyze a reaction where the reaction product accumulates within transduced cells. Since this enzyme is not present or not normally expressed in normal (non-transduced) host cells, there is little or no accumulation of the reaction product. (2) A "marker substrate" is chosen to match the "marker enzyme"; it is a compound that can be radiolabelled with appropriate isotopes for clinical imaging using gamma camera, SPECT or PET techniques, or is a paramagnetic compound appropriate for clinical magnetic resonance (MR) imaging. (3) The "marker substrate" must cross cell membranes readily, be metabolized by the "marker enzyme" and effectively trapped within transduced cells throughout the period of imaging, and must accumulate to levels that are measureable by existing clinical imaging techniques.

Selection of HSV1-tk as the "marker gene". To demonstrate feasibility and implementation of the above paradigm, model systems were established in tissue culture and experimental animals. The herpes simplex virus thymidine kinase gene (HSV1-tk) was selected as an example of a "marker gene", and three potential "marker substrates" for the enzyme HSV1 thymidine kinase (HSV1-TK) were evaluated. HSV1-tk has been extensively studied, and is currently being used as a drug susceptibility gene (in combination with ganciclovir) in clinical gene therapy protocols for the treatment of various tumors. These include five protocols for the treatment of brain tumors, and four other protocols for the treatment of leptomeningeal carcinomatosis, persistent head and neck cancer, advanced mesothelioma, and ovarian cancer [Clinical Protocol List, Cancer Gene Therapy, 4: 289–297 (1994)]. Thus, HSV1-tk can be viewed as both a "therapeutic gene" [Moolten, F. L., Cancer Res., 46: 5276–5281 (1986); Borrelli, E., Heyman, R., Hsi, M. & Evans, R. M., Proc. Natl. Acad. Sci. U.S.A., 85: 7572–7576 (1988); Moolten, F. L., & Wells, J. M., J. Natl. Cancer Inst., 82: 297–300 (1990); Culver, K. W., Ram, Z., Wallbridge, S., Ishii, H., Oldfield, E. H. & Blaese, R. M., Science, 256: 1550–1552 (1992)] as well as a "marker gene".

Choice of "marker substrates" for imaging HSV-TK expression. Three potential "marker substrates" for the HSV1-TK enzyme were evaluated: 5-iodo-2'-deoxy-uridine (IUdR) [Prusoff, W. H., Biochim. Biophys. Acta, 32: 295–296 (1959); MacCallum, F. O., & Juel-Jensen, B. E., Br. Med. J., 2 (517): 805–807 (1966); Buckley, T. F., & MacCallum, F. O., Br. Med. J., 2 (549): 419–420 (1967)], 9-(1,3-dihydroxy-2-propoxymethyl)-guanine (ganciclovir) [Smith, K. O., Galloway, K. S., Kennell, W. L., Ogilvie, K. K., & Radatus, B. K., Antimicrob. Agents Chemother., 22, 55–61 (1982); Smee, D. F., Martin, J.C., Verheyden, J. P. H., & Matthews, T. R., Antimicrob. Agents Chemother., 23: 676–682 (1983); Field, A. K., Davies, M. E., DeWitt, C., Perry, H. C., Liou, R., Germershausen, J., Karkas, J. D., Ashton, W. T., Johnston, D. B. R., & Tolman, R., Proc. Natl. Acad. Sci. U.S.A., 80: 4139–4143 (1983)], and 2'-fluoro-5-iodo-1-β-D-arabinofuranosyl-uracil (FIAU) [Watanabe, K. A., Reichman, U., Hirota, K., Lopez, C. & Fox, J. J., J. Med. Chem., 22, 21–24 (1979)]. These compounds were developed, and/or have been used as anti-viral agents; they are phosphorylated by the HSV1-TK enzyme and cause inhibition of viral DNA synthesis [Tovell, D. R., Yacyshin, H. P., Misra, H. K., Knaus, E. E., Wiebe, L. L., Samuel, J., Gill, J. M., & Tyrrell, D. L. J., J. Med. Virol., 22, 183–188 (1987); Grant, A. J., Feinberg, A., Chou, T.-C., Watanabe, K., Fox, J. J., & Philips, F. S., Biochem. Pharmacol., 31: 1103–1108 (1982); Kong, X.-B., Scheck, A., Price, R. W., Vidal, P. M., Fannuchi, M. P., Watanabe, K. A., Fox, J. J., & Chou, T.-C., Antiviral Research, 10: 153–166 (1988)]. These compounds can also be radiolabelled for noninvasive imaging. Radiolabelled IUdR has recently been used to image tumor proliferation because of its ability to incorporate into the DNA of dividing cells [Tjuvajev, J. G., Muraki, A., Ginos, J., Berg, J., Koutcher, J., Ballon, D., Beattie, B., Finn, R., & Biasberg, R. G., J. Nucl. Med., 34: 1152–1162 (1993); Tjuvajev, J. G., Macapinlac, H. A., Daghighian, Scott, A. M., Ginos, J. Z., Finn, R. D., Kothari, P., Desai, R., Zhang, J., Beattie, B., Graham, M., Larson, S., & Blasberg, R. G., J. Nucl. Med., 35: 1407–1417 (1994)]. Ganciclovir has been used in clinical gene therapy protocols for treatment of tumors transduced with HSV-tk gene [Clinical Protocol List, Cancer Gene Therapy, 4: 289–297 (1994)]. FIAU was chosen as a potential "marker substrate" because it is representative of 2'-fluoro-substituted nucleoside analogues and radiolabelled iodine can be incorporated into the molecule to facilitate imaging with gamma camera, SPECT and PET imaging techniques. Radiolabelled FIAU and other 2'-fluoro-substituted nucleoside analogues have been studied as potential agents for imaging HSV encephalitis [Saito, Y., Price, R. W., Rotenberg, D. A., Fox, J. J., Su, T. L., Watanabe, K. A., & Phillips, F. S., Science, 217: 1151–1153 (1982); Saito, Y., Rubenstein, R., Price, R. W., Fox, J. J., Watanabe, K. A., Ann. Neurol., 15: 548–558 (1984); Price, R. W., Cardle, K., & Watanabe, K. A., Cancer Res., 43: 3619–3627 (1983)]. FIAU has also been studied as a potential anti-neoplastic chemotherapeutic agent in patients [Feinberg, A., Leyland-Jones, B., Fanucchi, M., Hancock, C., Fox, J. J., Watanabe, K. A., Vidal, P. M., Williams, L., Young, C. W., Philips, F. S., Antimicrob. Agents and Chemother., 27: 733–738 (1985); King, D., Transplantation Proceedings, 23 (Suppl. 3): 168–170 (1991); Marshall, E., Science, 264: 1530 (1994)]. The 2'-fluoro substitution stabilizes the N-glucosidic bond against enzymatic cleavage by nucleoside phosphorylases [Abrams, D. N., Lee, Y. W., Mercer, J. R., Knaus, E. E., Wiebe, L. I., Br. J. Radiol., 59: 263–268 (1985)] and results in a significant prolongation of its half-life in plasma. The metabolic stability of FIAU accounts in part for its toxicity at pharmacologic doses [Feinberg, A., Leyland-Jones, B., Fanucchi, M., Hancock, C., Fox, J. J., Watanabe, K. A., Vidal, P. M., Williams, L., Young, C. W., Philips, F. S., Antimicrob. Agents and Chemother., 27: 733–738 (1985); King, D., Transplantation Proceedings, 23 (Suppl. 3): 168–170 (1991); Marshall, E., Science, 264: 1530 (1994)], but also makes it a more suitable imaging agent.

In vitro Studies. The sensitivity profiles for naive RG2 cells growing in ganciclovir containing media demonstrated an $ED_{50}$ of 0.2 mg/ml. Similar ganciclovir sensitivity profiles for the bulk culture of transduced RG2TK+ cells demonstrated an $ED_{50}$ of 0.001 mg/ml (FIG. 1A). The transduced RG2TK+ cells were approximately 200-fold more sensitive to ganciclovir than wild-type RG2 cells. The profiles of "high-sensitivity" RG2TK+ clone #16 and "low-sensitivity" clone #32 demonstrated a ganciclovir $ED_{50}$ of approximately 0.0002 mg/ml and 0.03 mg/ml, respectively (FIG. 1B). The high-sensitivity RG2TK+ clone #16 was 5-fold more sensitive to ganciclovir compared to the bulk culture of transfected RG2TK+ cells and approximately 1000-fold more sensitive to ganciclovir than wild-type RG2 cells.

Northern blot analysis of the mRNA from wild-type RG2 and RG2TK+ cell lines confirmed high level of expression of HSV1-tk gene in the bulk RG2TK+ cell line and the absence of HSV1-tk mRNA in naive RG2 cells (FIG. 2A). Substantially higher HSV1-tk gene expression level was observed in the high-sensitivity clone #16 compared to that in the low-sensitivity clone #32 (FIG. 2B). The vector-specific origin of RNA transcripts was confirmed by re-hybridization of the blot with the MoMLV-U3 specific probe (FIG. 2C).

The accumulation of 6-[$^3$H]-IUdR, 8-[$^3$H]-ganciclovir and 2-[$^{14}$C]-FIAU in bulk RG2TK+ transduced cells and in RG2 wild-type cells was measured and compared. Double-label studies were performed and all accumulation values were normalized to that of thymidine (2-[$^{14}$C]-TdR or methyl-[$^3$H]-TdR) in order to control for differences in cell proliferation in the different experiments (FIG. 5). The accumulation of ganciclovir by RG2TK+ cells was low compared to that of FIAU and IUdR; less than 5% and 3%, respectively (FIGS. 4A and 5B). Although the accumulation of IUdR by RG2TK+ cells was somewhat higher than that of FIAU in this system, the accumulation of IUdR does not distinguish between transduced RG2TK+ and non-transduced RG2 cells (FIGS. 4B and 5C).

Assessment of "marker substrates". In order to evaluate the proficiency of "marker substrates" for imaging of HSV1-tk expression, two parameters were developed: 1) "sensitivity", defined as the change in substrate uptake (normalized to TdR) divided by the change in HSV1-tk expression, and 2) "selectivity", defined as "sensitivity" divided by substrate uptake due to endogenous (mammalian) TK. These two related measures were considered useful for imaging considerations because the intensity of the images (e.g., high "sensitivity") and the ability to differentiate between HSV1-TK and endogenous-TK in the images (e.g., high "selectivity") are required. Note that the change in HSV1-tk expression was taken to be the difference in HSV1-tk mRNA/S28 RNA integrated optical density (IOD) ratios for RG2 and RG2TK+ (see FIG. 7B). It is important to note that this "selectivity" measure should not be interpreted as a relative sensitivity of the substrate to HSV1-TK vs. endogenous-TK (i.e. a value of 1 indicating equal sensitivity). Neither of the measures represents a fraction of some ideal value (i.e. they do not have a maximum of one). They are intended for the direct comparison of substrates only. A comparison of the "sensitivity" and "selectivity" of the three potential substrates for imaging HSV1-tk expression is shown in Table 1. It can be seen that: a) the "sensitivity" of ganciclovir is low and may not provide a sufficient signal for imaging; b) IUdR demonstrated intermediate "sensitivity", but very low "selectivity"; c) FIAU has the best "sensitivity" and "selectivity" for detecting HSV1-TK. Similar measures of "sensitivity" and "selectivity" can be obtained from animal data based on the accumulation of substrate (percent dose per gram tissue), rather than on data normalized to TdR as was done in the tissue culture studies (Tables 2 and 3).

Figure 7C:
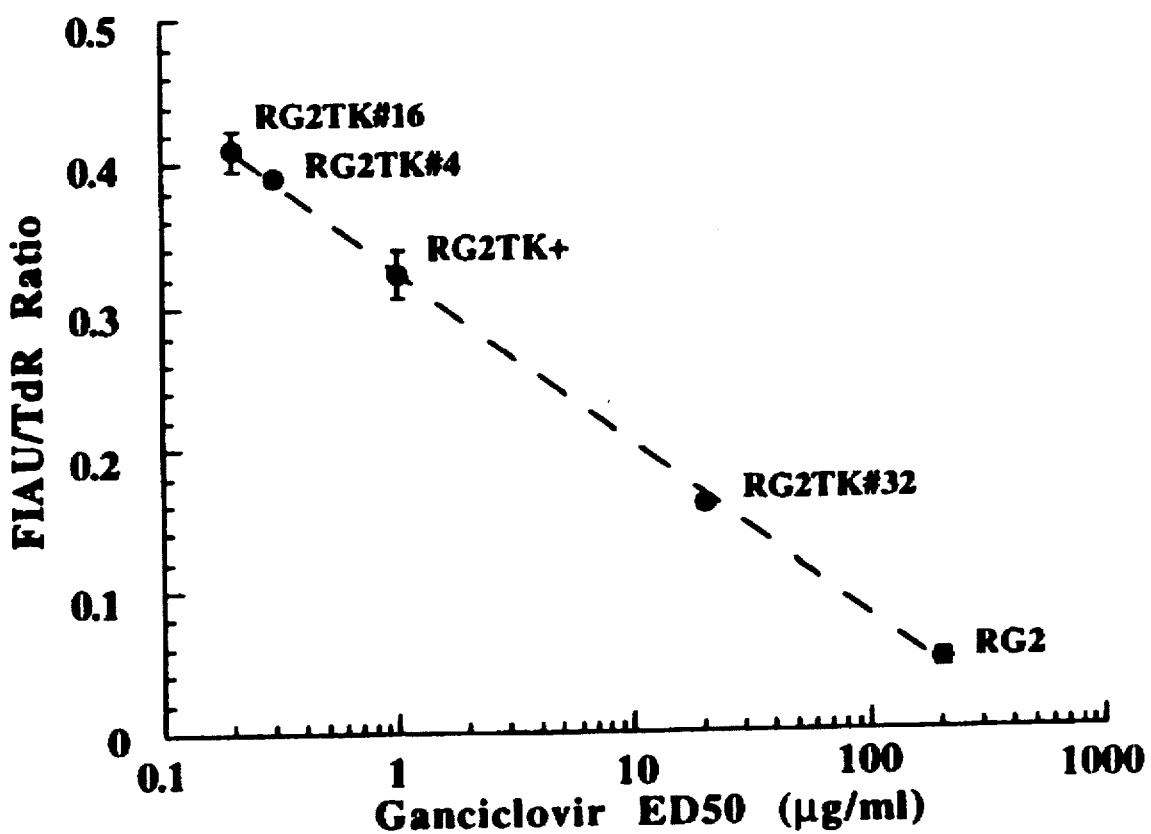

To assess whether the level of FIAU accumulation by transduced RG2TK+ cells reflects the level of HSV1-tk gene expression, FIAU accumulation was compared in different RG2TK+ clones with high and low sensitivity to ganciclovir and with different levels of HSV1-tk mRNA expression (FIG. 7). Highly significant relationships were observed between the normalized integrated optical density values of HSV1-tk mRNA and sensitivity to ganciclovir and FIAU accumulation in the different cell lines (FIGS. 7A and 7B). A highly significant inverse relationship was also observed between sensitivity to ganciclovir and FIAU uptake (FIG. 7C). These results indicate that the level of FIAU accumulation in different transduced cell lines correlates with the level of HSV1-tk expression.

In vivo Studies. On the basis of these results, FIAU was selected for imaging of HSV1-tk transduced tumors in vivo. RG2TK+ and RG2 tumors were produced in each hemisphere of the rat brain. The outline of the tumors is seen in the toluidine blue stained histological section (FIG. 10A). The RG2TK+ tumor is clearly seen in the autoradiographic image (FIG. 10B), whereas the RG2 tumor is barely detectable and the surrounding brain is at background levels. The punctate heterogeneous levels of FIAU activity observed in the RG2TK+ tumor (excluding the black areas representing tissue neurosis) are thought to reflect differences in HSV1-tk gene expression in the non-clonal, mixed population of transduced RG2TK+ cells growing intracerebrally. Quantitative analysis yielded mean activities of 0.180±0.140 and 0.022±0.024% dose/g for the RG2TK+ and RG2 tumors, respectively. Peak activity in the RG2TK+ tumor was 0.43% dose/g; adjacent brain activity was below the level of detection (<0.005% dose/g) on the autoradiograms. Rinsing tissue sections in acid solution (10% TCA) for 4 hours prior to X-ray film exposure had little effect on the distribution and amount of radioactivity measured in the autoradiogram (FIG. 10C). This can be seen by comparing the autoradiographic immages of adjacent tissue sections (FIGS. 10b and 10c) and indicates a very low background activity due to soluble radiolabelled metabolites. This demonstrates the value of using a "washout" imaging strategy (imaging 24 hours after FIAU administration) to reduce background radioactivity.

Other studies assessed whether FIAU imaging was sufficiently sensitive to monitor STK retroviral transduction of RG2 tumor cells in vivo. The HSV1-tk transduced tumor was well visualized on the autoradiographic image (FIG. 11B). In this case, the pattern of FIAU activity reflects spatial heterogeneity in the efficiency of transduction as well as differences in HSV1-tk gene expression. Surrounding normal brain and the area inoculated only with gp-STK-A2 vector-producer cells are poorly or not at all visualized. Histologic analysis of this area (FIG. 11A) showed an inflammatory reaction with perivascular infiltrates; the outlined area was heavily infiltrated and almost all vector-producer cells were rejected. Rinsing tissue sections in acid solution, prior to X-ray film exposure, as described above, had little effect on the distribution and amount of radioactivity measured in the transduced tumor, but eliminated the low level of radioactivity localized to the area of the left hemisphere that was inoculated with gp-STK-A2 vector-producer cells (FIG. 11C). Quantitative analysis yielded mean activities of 0.34±0.24% dose/g for the in vivo transduced RG2(TK+) and 0.028±0.023% dose/g for the gp-STK-A2 vector-producer cell inoculated area prior to rinsing. Peak activity in the in vivo transduced RG2(TK+) tumor was 0.96% dose/g; adjacent brain activity was below the level of detection (0.005% dose/g) on the autoradiograms.

These results demonstrate that the combination of HSV1-tk as a "marker gene" and radiolabeled FIAU as a "marker substrate" can be used to image successful gene transfer and expression. Metabolic stability of FIAU makes it a good radiotracer because it avoids problems associated with imaging confounding radiolabelled metabolites in both target and surrounding tissue. FIAU does have dose-limiting gastrointestinal, hematologic and neurotoxicity, and severe liver and pancreatic damage was observed in long term administration of FIAU in a recent clinical trial for treatment of HVB hepatitis [Marshall, E., Science, 264: 1530 (1994)]. The potential toxicity from administering tracer radiolabelled FIAU for diagnostic studies is remote since a no carrier-added procedure for iodine labeling of FIAU is available [Misra, H. K., Knaus, E. E., Wiebe, L. I., & Tyrrell, D. L., Appl. Radiat. Isot., 37: 901–905 (1986)]. Carrier-free $^{131}$I, $^{123}$I or $^{124}$I can be used in the synthesis of 5-[*I]-FIAU and SPECT or PET imaging can be performed in many nuclear medicine departments. Alternatively, other radiolabelled 2'-fluoro-substituted nucleosides could also be explored as "marker substrates" for imaging HSV1-tk gene expression. Particularly promising for imaging HSV1-TK transduced intracerebral tumors are 5-ethyl-2'-fluoro-1-β-D-ribofuranosyl-uracil (FERU), 5-ethyl-2'-fluoro-1-β-D-arabinofuranosyl-uracil (FEAU), 5-(2-iodovinyl)-2'-fluoro-1-β-D-ribofuranosyl-uracil (IVFRU) and 5-(2-iodovinyl)-2'-fluoro-1-β-D-arabinofuranosyl-uracil (IVFAU) because of their higher lipophilicity and better permeability through the blood-brain barrier than that of FAIU [Iwashina, T., Toyell, D. R., Xu, L., Tyrrell, L., Knauss, E. E., & Wiebe, L. L, Drug Design and Delivery, 3: 309–321 (1988)].

HSV1-tk could be used as both a "therapeutic gene" and "marker gene". In other cases where the "therapeutic" and "marker" genes may be different, both genes must be included in the same gene delivery vector. For example, the retroviral vector G1I2SvTk contains both HSV1-tk and human interleukin-2 (IL-2) genes, and has been used for treatment of 9L gliosarcomas in rats. In this case, HSV1-tk and IL-2 were used both as therapeutic genes for the induction of drug susceptibility and immunomodulation, respectively [Ram, Z., Walbridge, S., Heiss, J. D., Culver, K. W., Blaese, M., & Oldfield, E. H., J. Neurosurg., 80: 535–540 (1994)]. The HSV1-tk gene of this HSV1-tk/IL-2 retroviral construct could also be used as a "marker gene" for imaging. Another example is the mutant herpes simples virus-based gene delivery vector hRR3; hRR3 was constructed with the *E. Coli* lacZ reporter gene substituted for the ribonucleotase reductase gene (an RR deficient mutant HSV) [Boviatsis, E. J., Park, J. S., SenaiEsteves, M., Krame, M., Chase, M. Efird, J. T., Wei, M. X., Breakfield, X. O., & Chiocca, A. E., Cancer Res. 54: 5745–5751 (1994)]. The functioning HSV1-tk gene of the hRR3 vector can be used as a "marker gene" for imaging, and other therapeutic genes can be substituted for *E. Coli* lacZ reporter in this vector. Imaging based on the expression of the "marker" gene may not always reflect a comparable expression of the "therapeutic" gene. However, the distribution of cells (tissue/organs) in the body expressing the "marker" gene and identified by noninvasive imaging is likely to reflect a similar distribution of the "therapeutic" gene.

The subject invention therefore provides a method for imaging gene transfer and expression that is non-invasive, clinically applicable and can be readily implemented using existing clinical imaging techniques. This technique would facilitate the monitoring and evaluation of in vivo gene therapy in human subjects.

What is claimed is:

1. A method of detecting gene transfer to and expression in a target tissue of a host subject comprising:
    (a) delivering to the target tissue of the host subject a transfer vector containing a marker gene not naturally present in the host subject wherein the marker gene is selected from the group consisting of wild-type, mutant or genetically engineered herpes simplex virus-thymidine kinase gene, and wherein the transfer vector is introduced to cells of the target tissue, and the marker gene is expressed in the cells of the target tissue, thereby generating a marker gene product which accumulates only in the cells containing the transfer vector;
    (b) administering to the host subject a labeled marker substrate where cells expressing the marker gene product of step (a) metabolizes the labeled marker substrate to produce a labeled marker metabolite wherein the labeled marker substrate comprises a labeled 2'-fluoro-nucleoside analogue; and
    (c) non-invasively imaging the target tissue or cells containing the labeled marker metabolite after clearance of residual marker substrate not metabolized by the marker gene product from said host subject thereby detecting gene transfer to and expression in the target tissue.

2. The method of claim 1 further comprising waiting a time-period after step (b) sufficient to allow at least 67% of non-specific label derived from residual marker substrate not metabolized by the marker gene product to clear from the subject.

3. The method of claim 1 further comprising waiting a time-period after step (b) sufficient to allow at least 80% of non-specific label derived from residual marker substrate not metabolized by the marker gene product to clear from the subject.

4. The method of claim 1 further comprising waiting a time-period after step (b) sufficient to allow at least 90% of non-specific label derived from residual marker substrate not metabolized by the marker gene product to clear from the subject.

5. The method of claim 1 wherein the transfer vector is introduced to the cells of the target tissue by transduction.

6. The method of claim 1 wherein the marker substrate is labelled with a radioisotope suitable for imaging by positron emission tomography, gamma camera or single-photon emission computed tomography.

7. The method of claim 1 wherein the marker substrate and marker metabolite are compounds containing a stable-isotope nuclide selected from the group consisting of $^2H$, $^{13}C$, $^{15}N$ and $^{19}F$.

8. The method of claim 1 wherein the labelled marker metabolite is imaged by positron emission tomography.

9. The method of claim 1 wherein the labelled marker metabolite is imaged by gamma camera or single-photon emission computed tomography.

10. The method of claim 1 wherein the labelled marker metabolite is imaged by magnetic resonance imaging.

11. The method of claim 1 wherein the transfer vector is nonspecific, incorporates the marker gene and suitable transcription promoter and enhancer elements, and is selected from the group consisting of a virus, a plasmid, a liposome, and a cell.

12. The method of claim 11 wherein the cell is transfected with the marker gene and suitable transcription promoter and enhancer elements ex vivo prior to administration to the host subject.

13. The method of claim 1 wherein the labelled 2'-fluoro-nucleoside analogue is selected from a group consisting of 5-[$^{123}$I]-, 5-[$^{124}$I]- and 5-[$^{131}$I]-2'-fluoro-5-iodo-1β-D-arabinofuranosyl-uracil, 5-[$^{18}$F]-2'-fluoro-5-fluoro-1-β-D-arabinofuranosyl-uracil, 2-[$^{11}$I]-and 5-([$^{11}$C]-methyl)-2'-fluoro-5-methyl-1-β-D-arabinofuranosyl-uracil, 2-[$^{11}$C]- and 5-([$^{11}$C]-ethyl)-2'-fluoro-5-ethyl-1-β-D-arabinofuranosyl-uracil, 5-(2-[$^{18}$F]-ethyl)-2'-fluoro-5-(2-fluoro-ethyl)-1-β-D-arabinofuranosyl-uracil, 5-[$^{123}$I]-, 5-[$^{124}$I]- and 5-[$^{131}$I]-2'-fluoro-5-iodovinyl-1-β-D-arabinofuranosyl-uracil, 5-[$^{123}$I]-, 5-[$^{124}$I]- and 5-[$^{131}$I]-2'-fluoro-5-iodo-1-β-D-ribofuranosyl-uracil and 5-[$^{123}$I]-, 5-[$^{124}$I]- and 5-[$^{131}$I]-2'-fluoro-5-iodovinyl-1-β-D-ribofuranosyl-uracil.

* * * * *